(12) United States Patent
Tran et al.

(10) Patent No.: US 11,208,456 B2
(45) Date of Patent: Dec. 28, 2021

(54) ANTI-KRAS-$^{G12D}$ T CELL RECEPTORS

(71) Applicant: The United States of America, as represented by the Secretary, Department of Health and Human Services, Bethesda, MD (US)

(72) Inventors: Eric Tran, Portland, OR (US); Yong-Chen Lu, Rockville, MD (US); Anna Pasetto, Stockholm (SE); Paul F. Robbins, Chevy Chase, MD (US); Steven A. Rosenberg, Potomac, MD (US); Zhili Zheng, Gaithersburg, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/838,395

(22) Filed: Apr. 2, 2020

(65) Prior Publication Data
US 2020/0247869 A1 Aug. 6, 2020

Related U.S. Application Data

(62) Division of application No. 16/321,899, filed as application No. PCT/US2017/044615 on Jul. 31, 2017, now Pat. No. 10,611,816.

(60) Provisional application No. 62/369,883, filed on Aug. 2, 2016.

(51) Int. Cl.
| | | |
|---|---|---|
| C07K 14/82 | (2006.01) |
| A61P 35/00 | (2006.01) |
| A61K 38/00 | (2006.01) |
| C12N 15/85 | (2006.01) |
| C07K 14/725 | (2006.01) |
| G01N 33/574 | (2006.01) |

(52) U.S. Cl.
CPC .......... *C07K 14/7051* (2013.01); *A61P 35/00* (2018.01); *C07K 14/82* (2013.01); *C12N 15/85* (2013.01); *G01N 33/57407* (2013.01); *A61K 38/00* (2013.01); *C12N 2015/8518* (2013.01); *G01N 2333/7051* (2013.01)

(58) Field of Classification Search
None
See application file for complete search history.

(56) References Cited

U.S. PATENT DOCUMENTS

| | | | |
|---|---|---|---|
| 7,709,002 B1 | 5/2010 | Schlom et al. |
| 8,034,334 B2 | 10/2011 | Dudley et al. |
| 8,383,099 B2 | 2/2013 | Dudley et al. |
| 10,117,918 B2 | 11/2018 | Sabin et al. |
| 10,556,940 B2 | 2/2020 | Tran et al. |
| 2012/0244133 A1 | 9/2012 | Rosenberg et al. |
| 2014/0378389 A1 | 12/2014 | Robbins et al. |
| 2017/0304421 A1 | 10/2017 | Wang et al. |
| 2020/0148739 A1 | 5/2020 | Tran et al. |

FOREIGN PATENT DOCUMENTS

| | | | |
|---|---|---|---|
| GB | 2 328 689 A | 3/1999 |
| JP | 2001-514190 A | 9/2001 |
| JP | 2013-541332 A | 11/2013 |
| JP | 2014-528714 A | 10/2014 |
| JP | 2017-536825 A | 12/2017 |
| WO | WO 99/10382 | 3/1999 |
| WO | WO 2008/089053 A2 | 7/2008 |
| WO | WO 2015/022520 A1 | 2/2015 |
| WO | WO 2016/085904 A1 | 6/2016 |
| WO | WO 2017/048593 A1 | 3/2017 |

OTHER PUBLICATIONS

"Herwaroncancer", downloaded on Aug. 21, 2020 from URL:< http://herwaroncancer.com/cancer-prevention-and-awareness/>) (Year: 2020).*
U.S. Appl. No. 16/321,899, filed Jan. 30, 2019.
Bai et al., "Inference of high resolution HLA types using genome-wide RNA or DNA sequencing reads," *BMC Genomics*, 15: 325 (2014).
Cohen et al., "Enhanced antitumor activity of murine-human hybrid T-cell receptor (TCR) in human lymphocytes is associated with improved pairing and TCR/CD3 stability," *Cancer Res.*, 66: 8878-8886 (2006).
Cohen et al., "Enhanced antitumor activity of T cells engineered to express T-cell receptors with a second disulfide bond," *Cancer Res.*, 67: 3898-3903 (2007).
Dudley et al., "Adoptive cell transfer therapy following non-myeloablative but lymphodepleting chemotherapy for the treatment of patients with refractory metastatic melanoma," *J. Clin. Oncol.*, 23: 2346-2357 (2005).
Dudley et al., "Generation of tumor-infiltrating lymphocyte cultures for use in adoptive transfer therapy for melanoma patients," *J. Immunother.*, 26(4): 332-342 (2003).
Haga-Friedman et al., "Incorporation of transmembrane hydrophobic mutations in the TCR enhance its surface expression and T cell functional avidity," *J. Immunol.*, 188: 5538-5546 (2012).
International Bureau, International Search Report and Written Opinion in International Application No. PCT/US2017/044615, dated Dec. 20, 2017.
Lu et al., "Efficient identification of mutated cancer antigens recognized by T cells associated with durable tumor regressions," *Clin. Cancer Res.*, 20(13): 3401-3410 (2014).
National Center for Biotechnology Information, Protein Data Bank, 4OZI-E, downloaded on May 30, 2019.

(Continued)

*Primary Examiner* — Sergio Coffa
(74) *Attorney, Agent, or Firm* — Leydig, Voit & Mayer

(57) ABSTRACT

Disclosed is an isolated or purified T cell receptor (TCR) having antigenic specificity for mutated Kirsten rat sarcoma viral oncogene homolog (KRAS) presented in the context of an HLA-Cw*0802 molecule. Related polypeptides and proteins, as well as related nucleic acids, recombinant expression vectors, host cells, populations of cells, and pharmaceutical compositions are also provided. Also disclosed are methods of detecting the presence of cancer in a mammal and methods of treating or preventing cancer in a mammal.

36 Claims, 5 Drawing Sheets

Figure 2A:
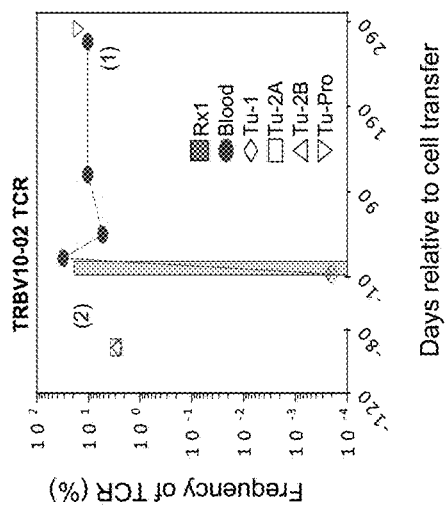
Figure 2B:
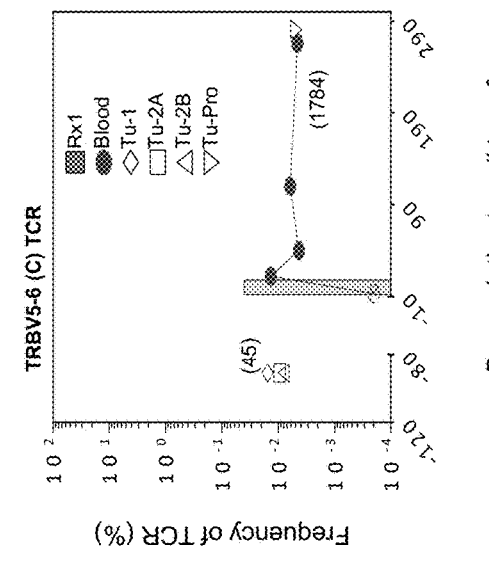
Figure 2C:
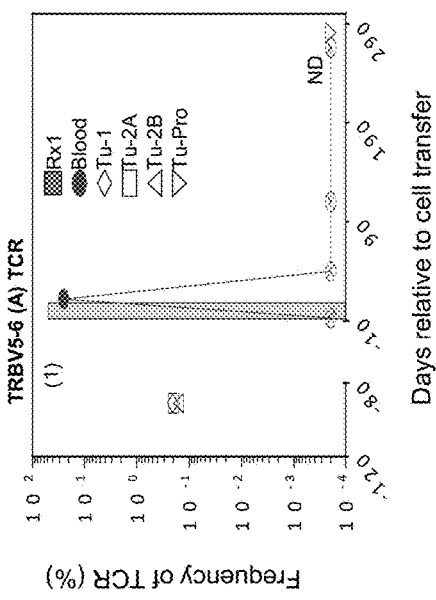
Figure 2D:
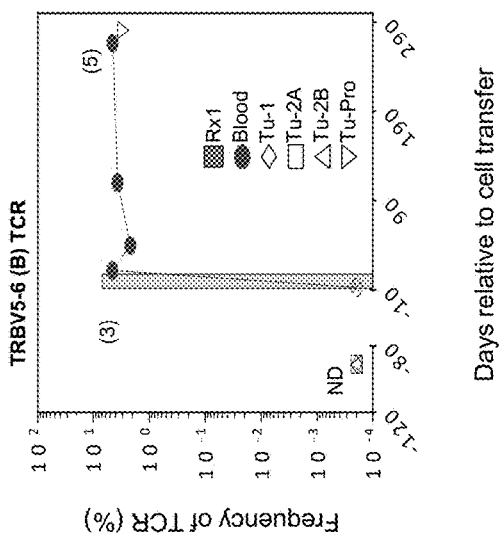
Figure 3A:
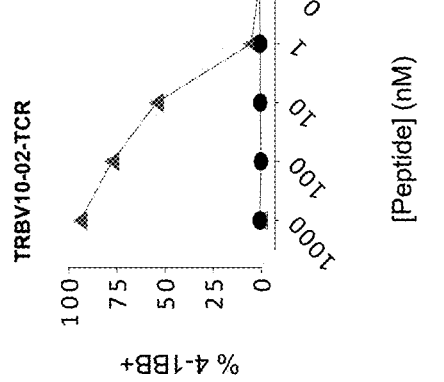
Figure 3B:
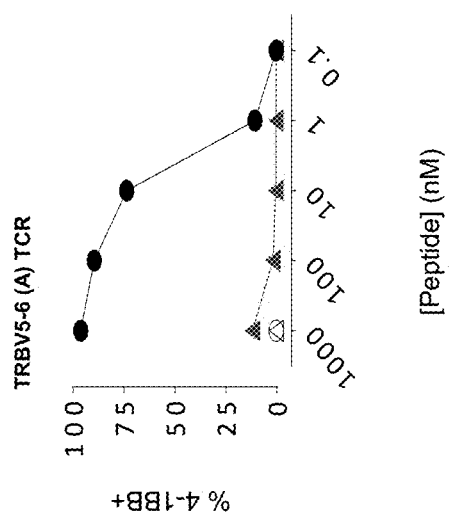
Figure 3C:
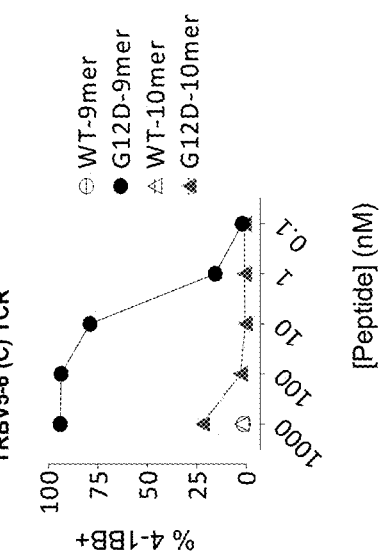
Figure 3D:
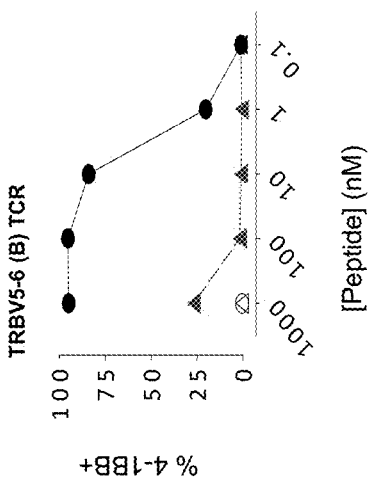

Specification includes a Sequence Listing.

(56) References Cited

OTHER PUBLICATIONS

Pasetto et al., "Tumor- and Neoantigen-Reactive T-cell Receptors Can Be Identified Based on Their Frequency in Fresh Tumor," *Cancer Immunol. Res.*, 4(9): 734-743 (2016).
Petersen et al., "T-cell receptor recognition of HLA-DQ2-gliadin complexes associated with celiac disease," *Nat. Struct. Mol. Biol.*, 21(5): 480-488 (2014).
Riddell et al., "The use of anti-CD3 and anti-CD28 monoclonal antibodies to clone and expand human antigen-specific T cells," *J. Immunol. Methods*, 128(2): 189-201 (1990).
Tran, E., "Targeting the human gastrointestinal cancer mutanome with adoptive T-cell therapy," Presentation given at BCCRC in Vancouver, BC on Jan. 4, 2016.
Tran et al., "Cancer immunotherapy based on mutation-specific CD4+ T cells in a patient with epithelial cancer," *Science*, 344: 641-645 (2014).
Tran et al., "Immunogenicity of somatic mutations in human gastrointestinal cancers," *Science*, 350(6266): 1387-1390 (2015).
Tran et al., "Immunogenicity of somatic mutations in human gastrointestinal cancers supplementary material," *Science*, 350(6266): 1387-1390 (2015).
Tran et al., "T-Cell Transfer Therapy Targeting Mutant KRAS in Cancer," *NEJM*, 375(23): 2255-2262 (2016).
Tran et al., "T-Cell Transfer Therapy Targeting Mutant KRAS in Cancer Supplementary Appendix," *NEJM*, 375(23): 2255-2262 (2016).
Wang et al., "Identification of T-cell Receptors Targeting KRAS-Mutated Human Tumors," *Cancer Immunol. Res.*, 4(3): 204-214 (2016).
"Evaluating Subject Matter Eligibility Under 35 U.S.C. § 101," Mar. 19, 2014 update, pp. 1-93 (2014).
"Government-Owned Inventions; Availability for Licensing," Notice published on Apr. 10, 2015 on the web at https://www.federalregister.gov/articles/2015/04/10/2015-08290/government-owned-inventions-availability-for-licensing.
Abrams et al., "Identification of overlapping epitopes in mutant ras oncogene peptides that activate CD4+ and CD8+ T cell responses," *European Journal of Immunology*, 26(2):435-443 (Feb. 1, 1996).
Abrams et al., "Generation of Stable CD4+ and CD8+ T Cell Lines from Patients Immunized with ras Oncogene-Derived Peptides Reflecting Codon 12 Mutations," *Cellular Immunology*, 182:137-151 (1997).
Anonymous "Uniprot: A0A075B5I2," Retrieved from http://ibis.internal.epo.org/exam/dbfetch.jsp?id=UNIPROT:A0A075B5I2 (Oct. 1, 2014).
Anonymous "Uniprot: Q5R1F9", Retrieved from http://ibis.internal.epo.org/exam/dbfetch.jsp?id=UNIPROT:Q5R1F9 (Jan. 4, 2005).
Bergmann-Leitner et al., "Identification of a Human CD8+ T Lymphocyte Neo-epitope Created by a *ras* Codon 12 Mutation Which is Restricted by the HLA-A2 Allele," *Cellular Immunology*, 187:103-116 (1998).
Bonehill et al., "Messenger RNA-electroporated dendritic cells presenting MAGE-A3 simultaneously in HLA class I and class II molecules," *J. Immunol.*, 172(11): 6649-6657 (2004).
Bristol et al., "Identification of a ras oncogene peptide that contains both CD4(+) and CD8(+) T cell epitopes in a nested configuration and elicits both T cell subset responses by peptide or DNA immunization," *Cellular Immunol.*, 205(2): 73-83 (2000).
Cohen et al., "T-Cell Receptor-Like Antibodies: Targeting the Intracellular Proteome Therapeutic Potential and Clinical Applications," *Antibodies*, 2:517-534 (2013).
Fujii et al., "Clinical significance of *KRAS* gene mutation and epidermal growth factor receptor expression in Japanese patients with squamous cell carcinoma of the larynx, oropharynx and hypopharynx," *Int. J. Clin. Oncol.* (2013) 18:454-463 (2013).
Gaudernack "T cell responses against mutant ras: a basis for novel cancer vaccines," *Immunotechnology*, 2(1): 3-9 (Feb. 1996).

Gjertsen et al., "HLA-A3 restricted mutant ras specific cytotoxic T-lymphocytes induced by vaccination with T-helper epitopes," *J. Mol. Med.*, 81 (1): 43-50 (2003).
Graef et al., "KIR2DS4 is a product of gene conversion with KIR3DL2 that introduced specificity for HLA-A*11 while diminishing avidity for HLA-C," *J. Exp. Med.* Oct. 26, 2009; 206(11):2557-72 and pp. S1-S6 (2009).
Gros et al., "PD-1 identifies the patient-specific CD8+ tumor-reactive repertoire infiltrating human tumors," *J. Clin. Invest.*, 124(5): 2246-2259 (2014).
He et al., "*Ras* gene mutations in Chinese Leukaemia patients and members of a family with high incidence of Leukaemia," *Leuk Res.* Nov-Dec. 1996; 20 (11-12):901-3 (1996).
He et al., "The relationship between *KRAS* gene mutations and HLA class I antigen downregulations in the metastasis of non-small cell lung cancer," *J. Int. Med.* Res. Oct. 2013;41(5): 1473-83 (2013).
International Bureau, International Search Report and Written Opinion in International Application No. PCT/US2015/062269, dated Mar. 7, 2016.
International Bureau, International Search Report and Written Opinion in International Application No. PCT/US2016/050875, dated Nov. 11, 2016.
Japanese Patent Office, Official Action in counterpart Japanese Patent Application No. 513423/2018, dated Sep. 8, 2020.
Jin et al., "Simplified method of the growth of human tumor infiltrating lymphocytes in gas-permeable flasks to numbers needed for patient treatment," *J. Immunother.*, 35(3): 283-292 (2012).
Jones et al., "Frequent mutations of chromatin remodeling gene ARID1A in ovarian clear cell carcinoma," *Science*, 330(6001): 228-231 (2010).
Kompier et al., "*FGFR3, HRAS, KRAS, NRAS and PIK3CA* mutations in bladder cancer and their potential as biomarkers for surveillance and therapy," PLoS One, Nov. 3, 2010;5 (11):e13821 (2010).
Kubuschok et al., "Naturally occurring T-cell response against mutated p21 ras oncoprotein in pancreatic cancer," *Clin. Cancer Res.*, 12(4): 1365-1372 (2006).
Lindinger et al., "Induction of Murine ras Ocogene Peptide-Specific T Cell Responses by Immunization with Plasmid DNA-based Minigene Vectors," Vaccine, 21 (27-30): 4285-4296, (2003).
Memorandum from Deputy Commissioner for Patent Examination Policy Andrew H. Hirshfeld, dated Mar. 4, 2014, 19 pages in total with first page not numbered. (2014).
McKinney, "Brain Tumors: Incidence, survival, and aetiology," *J. Neurosurg. Psychiatry* 2004;75(Suppl II):ii12-ii17 (2004).
Prigge et al., "No evidence of oncogenic KRAS mutations in squamous cell carcinomas of the anogenital tract and head and neck region independent of human papillomavirus and p16INK4a status," *Human Pathology* (2014) 45, 2347-2354 (2014).
Qin et al., "CD4+ T-cell immunity to mutated ras protein in pancreatic and colon cancer patients," *Cancer Res.*, 55(14): 2984-2987 (1995).
Rosenberg, "T cells as a Drug for the Personalized Immunotherapy of Cancer," *The Inaugural International Cancer Immunother. Conf.*, Sep. 16, 2015.
Rosenberg et al., "Adoptive cell transfer as personalized immunotherapy for human cancer," *Science*, 348(6230): 62-68 (2015).
Shono et al., "Specific T-cell immunity against Ki-ras peptides in patients with pancreatic and colorectal cancers," *Br. J. Cancer*, 88(4): 530-536 (2003).
Tran, "Cell transfer therapy against somatic mutations in human gastrointestinal cancers," presentation given at 8th Annual Canadian Cancer Immunotherapy Consortium (CICC) Meeting in Vancouver, BC on May 21, 2015.
Tran, "Immunogenicity and immunotherapeutic targeting of somatic mutations inhuman gastrointestinal cancers," presentation given at 15th Annual CCR Fellows and Young Investigators Colloquium at the NCI in Shady Grove, MD on Mar. 23, 2015.
Tran, "Immunogenicity and immunotherapeutic targeting of somatic mutations in human gastrointestinal cancers," presentation given during a visit to Ottawa Hospital Research Institute, Ottawa, ON, on Jul. 10, 2015.

(56) References Cited

OTHER PUBLICATIONS

Tsai et al., "K-Ras4A splice variant is widely expressed in cancer and uses a hybrid membrane-targeting motif," *PNAS*, 112(3): 779-784 (2015).

Warren et al., "A census of predicted mutational epitopes suitable for immunologic cancer control," *Human Immunol.*, 71: 245-254 (2010).

* cited by examiner

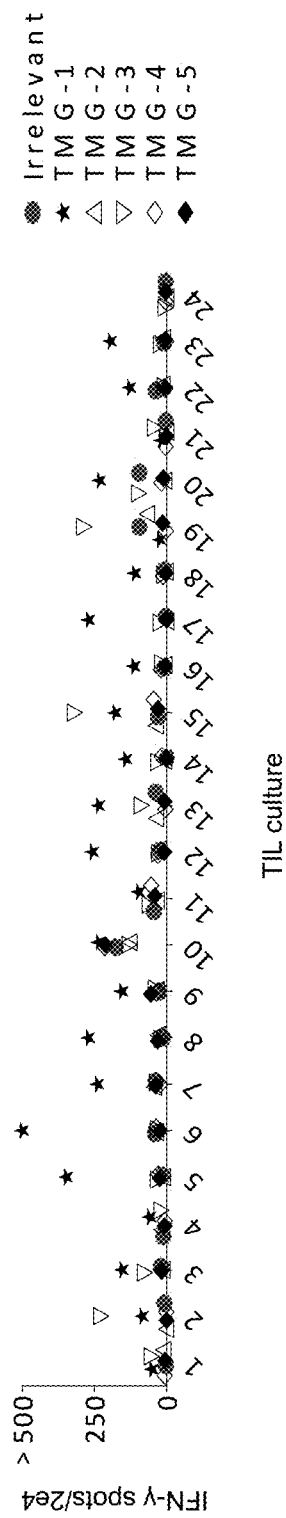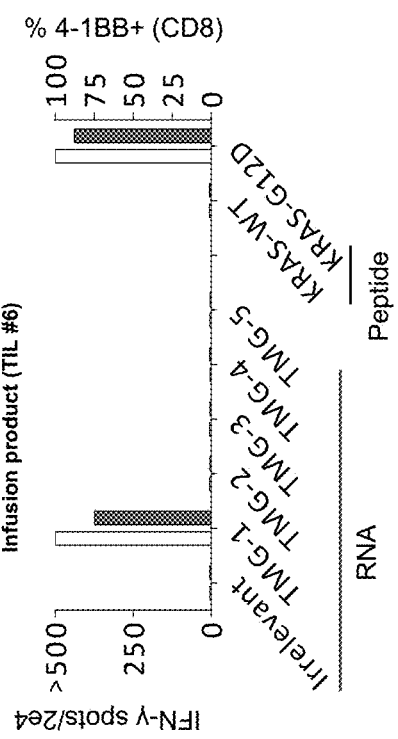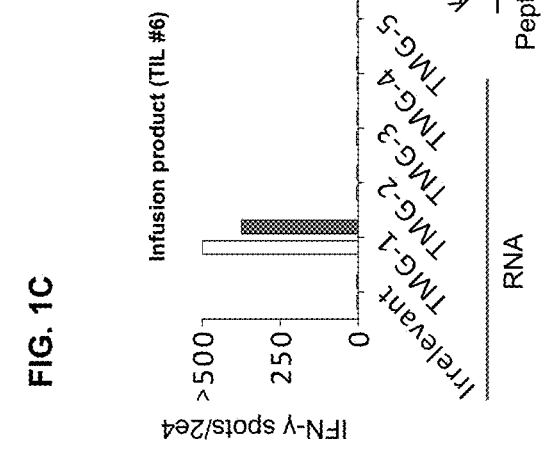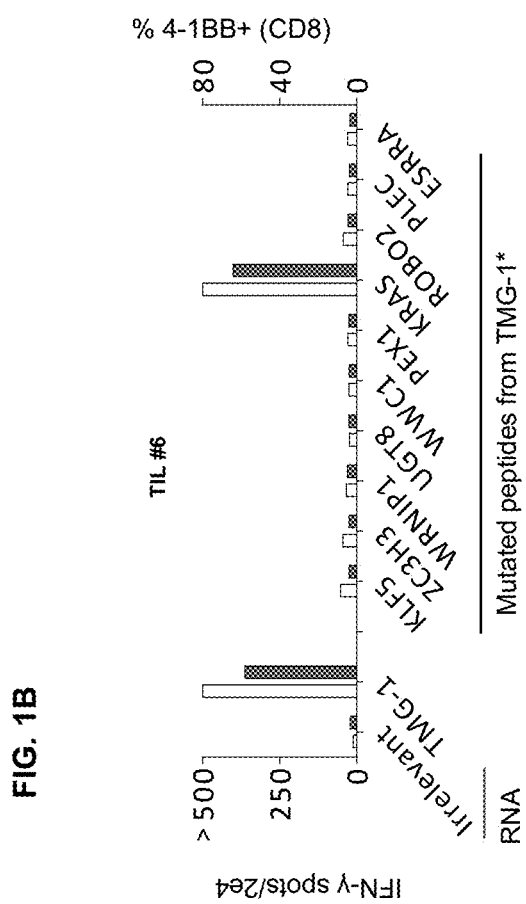
FIG. 1A
FIG. 1B
FIG. 1C

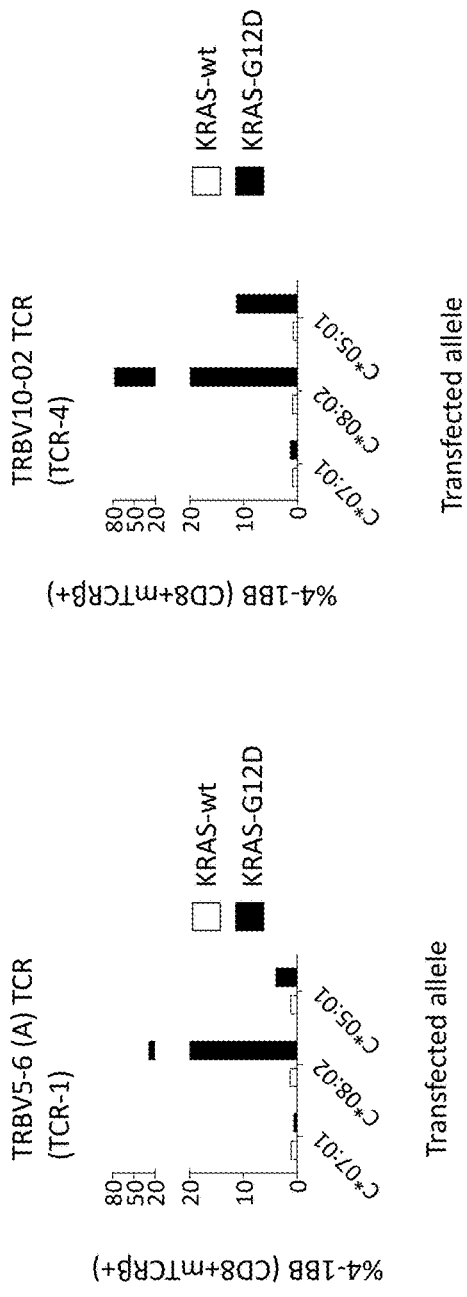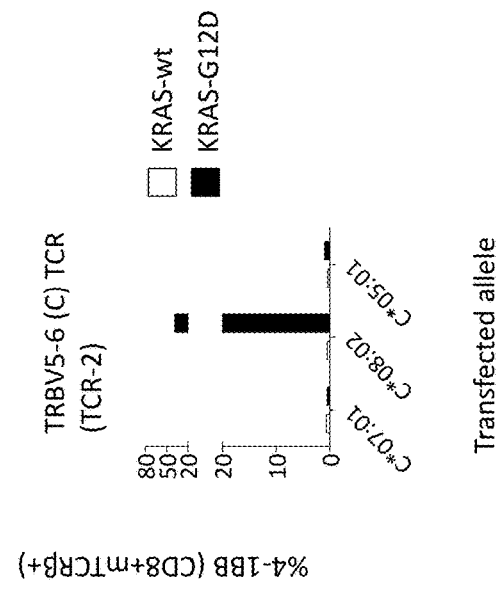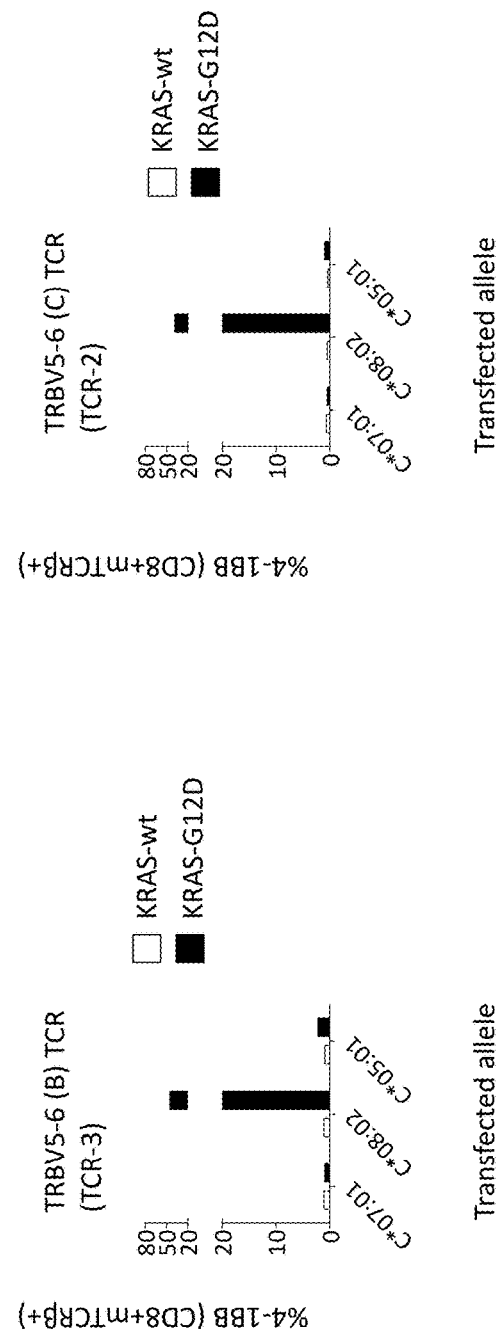
FIG. 5A
FIG. 5B
FIG. 5C
FIG. 5D

SEQUENCE LISTING

<160> NUMBER OF SEQ ID NOS: 70

<210> SEQ ID NO 1
<211> LENGTH: 189
<212> TYPE: PRT
<213> ORGANISM: Homo sapiens

<400> SEQUENCE: 1

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 2
<211> LENGTH: 188
<212> TYPE: PRT
<213> ORGANISM: Homo sapiens

<400> SEQUENCE: 2

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr

```
                130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
                180                 185
```

<210> SEQ ID NO 3
<211> LENGTH: 189
<212> TYPE: PRT
<213> ORGANISM: Homo sapiens

<400> SEQUENCE: 3

```
Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185
```

<210> SEQ ID NO 4
<211> LENGTH: 188
<212> TYPE: PRT
<213> ORGANISM: Homo sapiens

<400> SEQUENCE: 4

```
Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
```

```
                    85                  90                  95
Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
                180                 185

<210> SEQ ID NO 5
<211> LENGTH: 10
<212> TYPE: PRT
<213> ORGANISM: Homo sapiens

<400> SEQUENCE: 5

Gly Ala Gly Gly Val Gly Lys Ser Ala Leu
1               5                   10

<210> SEQ ID NO 6
<211> LENGTH: 10
<212> TYPE: PRT
<213> ORGANISM: Homo sapiens

<400> SEQUENCE: 6

Gly Ala Asp Gly Val Gly Lys Ser Ala Leu
1               5                   10

<210> SEQ ID NO 7
<211> LENGTH: 9
<212> TYPE: PRT
<213> ORGANISM: Homo sapiens

<400> SEQUENCE: 7

Gly Ala Gly Gly Val Gly Lys Ser Ala
1               5

<210> SEQ ID NO 8
<211> LENGTH: 9
<212> TYPE: PRT
<213> ORGANISM: Homo sapiens

<400> SEQUENCE: 8

Gly Ala Asp Gly Val Gly Lys Ser Ala
1               5

<210> SEQ ID NO 9
<211> LENGTH: 7
<212> TYPE: PRT
<213> ORGANISM: Homo sapiens

<400> SEQUENCE: 9

Asn Ile Ala Thr Asn Asp Tyr
1               5

<210> SEQ ID NO 10
<211> LENGTH: 5
<212> TYPE: PRT
```

```
<213> ORGANISM: Homo sapiens

<400> SEQUENCE: 10

Gly Tyr Lys Thr Lys
1               5

<210> SEQ ID NO 11
<211> LENGTH: 15
<212> TYPE: PRT
<213> ORGANISM: Homo sapiens

<400> SEQUENCE: 11

Cys Leu Val Gly Asp Met Asp Gln Ala Gly Thr Ala Leu Ile Phe
1               5                   10                  15

<210> SEQ ID NO 12
<211> LENGTH: 5
<212> TYPE: PRT
<213> ORGANISM: Homo sapiens

<400> SEQUENCE: 12

Ser Gly His Asp Thr
1               5

<210> SEQ ID NO 13
<211> LENGTH: 6
<212> TYPE: PRT
<213> ORGANISM: Homo sapiens

<400> SEQUENCE: 13

Tyr Tyr Glu Glu Glu Glu
1               5

<210> SEQ ID NO 14
<211> LENGTH: 15
<212> TYPE: PRT
<213> ORGANISM: Homo sapiens

<400> SEQUENCE: 14

Cys Ala Ser Ser Leu Gly Glu Gly Arg Val Asp Gly Tyr Thr Phe
1               5                   10                  15

<210> SEQ ID NO 15
<211> LENGTH: 129
<212> TYPE: PRT
<213> ORGANISM: Homo sapiens

<400> SEQUENCE: 15

Met Arg Gln Val Ala Arg Val Ile Val Phe Leu Thr Leu Ser Thr
1               5                   10                  15

Ser Leu Ala Lys Thr Thr Gln Pro Ile Ser Met Asp Ser Tyr Glu Gly
                20                  25                  30

Gln Glu Val Asn Ile Thr Cys Ser His Asn Asn Ile Ala Thr Asn Asp
            35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Gly Asp Met Asp Gln
                100                 105                 110
```

Ala Gly Thr Ala Leu Ile Phe Gly Lys Gly Thr Thr Leu Ser Val Ser
        115                 120                 125

Ser

<210> SEQ ID NO 16
<211> LENGTH: 133
<212> TYPE: PRT
<213> ORGANISM: Homo sapiens

<400> SEQUENCE: 16

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Glu Leu Asn
                85                  90                  95

Val Asn Ala Leu Leu Leu Gly Asp Ser Ala Leu Tyr Leu Cys Ala Ser
            100                 105                 110

Ser Leu Gly Glu Gly Arg Val Asp Gly Tyr Thr Phe Gly Ser Gly Thr
        115                 120                 125

Arg Leu Thr Val Val
    130

<210> SEQ ID NO 17
<211> LENGTH: 7
<212> TYPE: PRT
<213> ORGANISM: Homo sapiens

<400> SEQUENCE: 17

Asn Ile Ala Thr Asn Asp Tyr
1               5

<210> SEQ ID NO 18
<211> LENGTH: 5
<212> TYPE: PRT
<213> ORGANISM: Homo sapiens

<400> SEQUENCE: 18

Gly Tyr Lys Thr Lys
1               5

<210> SEQ ID NO 19
<211> LENGTH: 15
<212> TYPE: PRT
<213> ORGANISM: Homo sapiens

<400> SEQUENCE: 19

Cys Leu Val Gly Asp Met Asp Gln Ala Gly Thr Ala Leu Ile Phe
1               5                   10                  15

<210> SEQ ID NO 20
<211> LENGTH: 5
<212> TYPE: PRT
<213> ORGANISM: Homo sapiens

<400> SEQUENCE: 20

Ser Gly His Asp Thr
1               5

<210> SEQ ID NO 21
<211> LENGTH: 6
<212> TYPE: PRT
<213> ORGANISM: Homo sapiens

<400> SEQUENCE: 21

Tyr Tyr Glu Glu Glu Glu
1               5

<210> SEQ ID NO 22
<211> LENGTH: 15
<212> TYPE: PRT
<213> ORGANISM: Homo sapiens

<400> SEQUENCE: 22

Cys Ala Ser Ser Leu Gly Arg Ala Ser Asn Gln Pro Gln His Phe
1               5                  10                  15

<210> SEQ ID NO 23
<211> LENGTH: 129
<212> TYPE: PRT
<213> ORGANISM: Homo sapiens

<400> SEQUENCE: 23

Met Arg Gln Val Ala Arg Val Ile Val Phe Leu Thr Leu Ser Thr Leu
1               5                   10                  15

Ser Leu Ala Lys Thr Thr Gln Pro Ile Ser Met Asp Ser Tyr Glu Gly
                20                  25                  30

Gln Glu Val Asn Ile Thr Cys Ser His Asn Asn Ile Ala Thr Asn Asp
            35                  40                  45

Tyr Ile Thr Trp Tyr Gln Phe Pro Ser Gln Gly Pro Arg Phe Ile
        50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Gly Asp Met Asp Gln
                100                 105                 110

Ala Gly Thr Ala Leu Ile Phe Gly Lys Gly Thr Thr Leu Ser Val Ser
            115                 120                 125

Ser

<210> SEQ ID NO 24
<211> LENGTH: 133
<212> TYPE: PRT
<213> ORGANISM: Homo sapiens

<400> SEQUENCE: 24

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
                20                  25                  30

Thr Arg Gly Gln Gln Val Thr Leu Arg Cys Ser Pro Lys Ser Gly His
            35                  40                  45

```
Asp Thr Val Ser Trp Tyr Gln Gln Ala Leu Gly Gln Gly Pro Gln Phe
         50                  55                  60

Ile Phe Gln Tyr Tyr Glu Glu Glu Arg Gln Arg Gly Asn Phe Pro
 65                  70                  75                  80

Asp Arg Phe Ser Gly His Gln Phe Pro Asn Tyr Ser Ser Glu Leu Asn
                 85                  90                  95

Val Asn Ala Leu Leu Leu Gly Asp Ser Ala Leu Tyr Leu Cys Ala Ser
            100                 105                 110

Ser Leu Gly Arg Ala Ser Asn Gln Pro Gln His Phe Gly Asp Gly Thr
            115                 120                 125

Arg Leu Ser Ile Leu
            130

<210> SEQ ID NO 25
<211> LENGTH: 7
<212> TYPE: PRT
<213> ORGANISM: Homo sapiens

<400> SEQUENCE: 25

Asn Ile Ala Thr Asn Asp Tyr
 1               5

<210> SEQ ID NO 26
<211> LENGTH: 5
<212> TYPE: PRT
<213> ORGANISM: Homo sapiens

<400> SEQUENCE: 26

Gly Tyr Lys Thr Lys
 1               5

<210> SEQ ID NO 27
<211> LENGTH: 15
<212> TYPE: PRT
<213> ORGANISM: Homo sapiens

<400> SEQUENCE: 27

Cys Leu Val Gly Asp Arg Asp Gln Ala Gly Thr Ala Leu Ile Phe
 1               5                  10                  15

<210> SEQ ID NO 28
<211> LENGTH: 5
<212> TYPE: PRT
<213> ORGANISM: Homo sapiens

<400> SEQUENCE: 28

Ser Gly His Asp Thr
 1               5

<210> SEQ ID NO 29
<211> LENGTH: 6
<212> TYPE: PRT
<213> ORGANISM: Homo sapiens

<400> SEQUENCE: 29

Tyr Tyr Glu Glu Glu Glu
 1               5

<210> SEQ ID NO 30
<211> LENGTH: 15
<212> TYPE: PRT
<213> ORGANISM: Homo sapiens
```

```
<400> SEQUENCE: 30

Cys Ala Ser Ser Phe Gly Gln Ser Ser Thr Tyr Gly Tyr Thr Phe
1               5                   10                  15

<210> SEQ ID NO 31
<211> LENGTH: 129
<212> TYPE: PRT
<213> ORGANISM: Homo sapiens

<400> SEQUENCE: 31

Met Arg Gln Val Ala Arg Val Ile Val Phe Leu Thr Leu Ser Thr Leu
1               5                   10                  15

Ser Leu Ala Lys Thr Thr Gln Pro Ile Ser Met Asp Ser Tyr Glu Gly
                20                  25                  30

Gln Glu Val Asn Ile Thr Cys Ser His Asn Asn Ile Ala Thr Asn Asp
            35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Gly Asp Arg Asp Gln
            100                 105                 110

Ala Gly Thr Ala Leu Ile Phe Gly Lys Gly Thr Thr Leu Ser Val Ser
        115                 120                 125

Ser

<210> SEQ ID NO 32
<211> LENGTH: 133
<212> TYPE: PRT
<213> ORGANISM: Homo sapiens

<400> SEQUENCE: 32

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
                20                  25                  30

Thr Arg Gly Gln Gln Val Thr Leu Arg Cys Ser Pro Lys Ser Gly His
            35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Phe Gly Gln Ser Ser Thr Tyr Gly Tyr Thr Phe Gly Ser Gly Thr
        115                 120                 125

Arg Leu Thr Val Val
        130

<210> SEQ ID NO 33
<211> LENGTH: 6
<212> TYPE: PRT
<213> ORGANISM: Homo sapiens
```

```
<400> SEQUENCE: 33

Asp Arg Gly Ser Gln Ser
1               5

<210> SEQ ID NO 34
<211> LENGTH: 6
<212> TYPE: PRT
<213> ORGANISM: Homo sapiens

<400> SEQUENCE: 34

Ile Tyr Ser Asn Gly Asp
1               5

<210> SEQ ID NO 35
<211> LENGTH: 13
<212> TYPE: PRT
<213> ORGANISM: Homo sapiens

<400> SEQUENCE: 35

Cys Ala Ala Ala Met Asp Ser Ser Tyr Lys Leu Ile Phe
1               5                   10

<210> SEQ ID NO 36
<211> LENGTH: 5
<212> TYPE: PRT
<213> ORGANISM: Homo sapiens

<400> SEQUENCE: 36

Trp Ser His Ser Tyr
1               5

<210> SEQ ID NO 37
<211> LENGTH: 6
<212> TYPE: PRT
<213> ORGANISM: Homo sapiens

<400> SEQUENCE: 37

Ser Ala Ala Ala Asp Ile
1               5

<210> SEQ ID NO 38
<211> LENGTH: 12
<212> TYPE: PRT
<213> ORGANISM: Homo sapiens

<400> SEQUENCE: 38

Cys Ala Ser Ser Asp Pro Gly Thr Glu Ala Phe Phe
1               5                   10

<210> SEQ ID NO 39
<211> LENGTH: 132
<212> TYPE: PRT
<213> ORGANISM: Homo sapiens

<400> SEQUENCE: 39

Met Lys Ser Leu Arg Val Leu Val Ile Leu Trp Leu Gln Leu Ser
1               5                   10                  15

Trp Val Trp Ser Gln Gln Lys Glu Val Glu Gln Asn Ser Gly Pro Leu
                20                  25                  30

Ser Val Pro Glu Gly Ala Ile Ala Ser Leu Asn Cys Thr Tyr Ser Asp
            35                  40                  45

Arg Gly Ser Gln Ser Phe Phe Trp Tyr Arg Gln Tyr Ser Gly Lys Ser
```

```
                50                  55                  60
Pro Glu Leu Ile Met Phe Ile Tyr Ser Asn Gly Asp Lys Glu Asp Gly
 65                  70                  75                  80

Arg Phe Thr Ala Gln Leu Asn Lys Ala Ser Gln Tyr Val Ser Leu Leu
                     85                  90                  95

Ile Arg Asp Ser Gln Pro Ser Asp Ser Ala Thr Tyr Leu Cys Ala Ala
                100                 105                 110

Ala Met Asp Ser Ser Tyr Lys Leu Ile Phe Gly Ser Gly Thr Arg Leu
                115                 120                 125

Leu Val Arg Pro
    130

<210> SEQ ID NO 40
<211> LENGTH: 130
<212> TYPE: PRT
<213> ORGANISM: Homo sapiens

<400> SEQUENCE: 40

Met Gly Thr Arg Leu Phe Phe Tyr Val Ala Leu Cys Leu Leu Trp Ala
 1               5                  10                  15

Gly His Arg Asp Ala Gly Ile Thr Gln Ser Pro Arg Tyr Lys Ile Thr
                20                  25                  30

Glu Thr Gly Arg Gln Val Thr Leu Met Cys His Gln Thr Trp Ser His
            35                  40                  45

Ser Tyr Met Phe Trp Tyr Arg Gln Asp Leu Gly His Gly Leu Arg Leu
        50                  55                  60

Ile Tyr Tyr Ser Ala Ala Ala Asp Ile Thr Asp Lys Gly Glu Val Pro
 65                  70                  75                  80

Asp Gly Tyr Val Val Ser Arg Ser Lys Thr Glu Asn Phe Pro Leu Thr
                 85                  90                  95

Leu Glu Ser Ala Thr Arg Ser Gln Thr Ser Val Tyr Phe Cys Ala Ser
                100                 105                 110

Ser Asp Pro Gly Thr Glu Ala Phe Phe Gly Gln Gly Thr Arg Leu Thr
                115                 120                 125

Val Val
    130

<210> SEQ ID NO 41
<211> LENGTH: 141
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 41

Xaa Ile Gln Asn Pro Asp Pro Ala Val Tyr Gln Leu Arg Asp Ser Lys
 1               5                  10                  15

Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
        50                  55                  60

Trp Ser Asn Lys Ser Asp Phe Ala Cys Ala Asn Ala Phe Asn Asn Ser
 65                  70                  75                  80
```

```
Ile Ile Pro Glu Asp Thr Phe Phe Pro Ser Pro Glu Ser Ser Cys Asp
                85                  90                  95
Val Lys Leu Val Glu Lys Ser Phe Glu Thr Asp Thr Asn Leu Asn Phe
            100                 105                 110
Gln Asn Leu Ser Val Ile Gly Phe Arg Ile Leu Leu Leu Lys Val Ala
        115                 120                 125
Gly Phe Asn Leu Leu Met Thr Leu Arg Leu Trp Ser Ser
130                 135                 140
```

<210> SEQ ID NO 42
<211> LENGTH: 177
<212> TYPE: PRT
<213> ORGANISM: Homo sapiens

<400> SEQUENCE: 42

```
Glu Asp Leu Asn Lys Val Phe Pro Pro Glu Val Ala Val Phe Glu Pro
1               5                   10                  15
Ser Glu Ala Glu Ile Ser His Thr Gln Lys Ala Thr Leu Val Cys Leu
            20                  25                  30
Ala Thr Gly Phe Phe Pro Asp His Val Glu Leu Ser Trp Trp Val Asn
        35                  40                  45
Gly Lys Glu Val His Ser Gly Val Ser Thr Asp Pro Gln Pro Leu Lys
    50                  55                  60
Glu Gln Pro Ala Leu Asn Asp Ser Arg Tyr Cys Leu Ser Ser Arg Leu
65                  70                  75                  80
Arg Val Ser Ala Thr Phe Trp Gln Asn Pro Arg Asn His Phe Arg Cys
                85                  90                  95
Gln Val Gln Phe Tyr Gly Leu Ser Glu Asn Asp Glu Trp Thr Gln Asp
            100                 105                 110
Arg Ala Lys Pro Val Thr Gln Ile Val Ser Ala Glu Ala Trp Gly Arg
        115                 120                 125
Ala Asp Cys Gly Phe Thr Ser Val Ser Tyr Gln Gln Gly Val Leu Ser
    130                 135                 140
Ala Thr Ile Leu Tyr Glu Ile Leu Leu Gly Lys Ala Thr Leu Tyr Ala
145                 150                 155                 160
Val Leu Val Ser Ala Leu Val Leu Met Ala Met Val Lys Arg Lys Asp
                165                 170                 175
Phe
```

<210> SEQ ID NO 43
<211> LENGTH: 179
<212> TYPE: PRT
<213> ORGANISM: Homo sapiens

<400> SEQUENCE: 43

```
Glu Asp Leu Lys Asn Val Phe Pro Pro Glu Val Ala Val Phe Glu Pro
1               5                   10                  15
Ser Glu Ala Glu Ile Ser His Thr Gln Lys Ala Thr Leu Val Cys Leu
            20                  25                  30
Ala Thr Gly Phe Tyr Pro Asp His Val Glu Leu Ser Trp Trp Val Asn
        35                  40                  45
Gly Lys Glu Val His Ser Gly Val Ser Thr Asp Pro Gln Pro Leu Lys
    50                  55                  60
Glu Gln Pro Ala Leu Asn Asp Ser Arg Tyr Cys Leu Ser Ser Arg Leu
65                  70                  75                  80
Arg Val Ser Ala Thr Phe Trp Gln Asn Pro Arg Asn His Phe Arg Cys
```

```
                    85                  90                  95
Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 44
<211> LENGTH: 137
<212> TYPE: PRT
<213> ORGANISM: Mus musculus

<400> SEQUENCE: 44

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Thr
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135

<210> SEQ ID NO 45
<211> LENGTH: 173
<212> TYPE: PRT
<213> ORGANISM: Mus musculus

<400> SEQUENCE: 45

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95
```

```
His Gly Leu Ser Glu Glu Asp Lys Trp Pro Glu Gly Ser Pro Lys Pro
                100                 105                 110

Val Thr Gln Asn Ile Ser Ala Glu Ala Trp Gly Arg Ala Asp Cys Gly
            115                 120                 125

Ile Thr Ser Ala Ser Tyr Gln Gln Gly Val Leu Ser Ala Thr Ile Leu
130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 46
<211> LENGTH: 137
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (48)..(48)
<223> OTHER INFORMATION: Xaa is Thr or Cys
<220> FEATURE:
<221> NAME/KEY: MISC_FEATURE
<222> LOCATION: (112)..(112)
<223> OTHER INFORMATION: Xaa is Ser, Ala, Val, Leu, Ile, Pro, Phe, Met,
      or Trp
<220> FEATURE:
<221> NAME/KEY: MISC_FEATURE
<222> LOCATION: (114)..(114)
<223> OTHER INFORMATION: Xaa is Met, Ala, Val, Leu, Ile, Pro, Phe, or
      Trp
<220> FEATURE:
<221> NAME/KEY: MISC_FEATURE
<222> LOCATION: (115)..(115)
<223> OTHER INFORMATION: Xaa is Gly, Ala, Val, Leu, Ile, Pro, Phe, Met,
      or Trp

<400> SEQUENCE: 46

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Xaa
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Xaa
                100                 105                 110

Val Xaa Xaa Leu Arg Ile Leu Leu Leu Lys Val Ala Gly Phe Asn Leu
            115                 120                 125

Leu Met Thr Leu Arg Leu Trp Ser Ser
        130                 135

<210> SEQ ID NO 47
<211> LENGTH: 173
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (57)..(57)
<223> OTHER INFORMATION: Xaa is Ser or Cys

<400> SEQUENCE: 47
```

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Xaa Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

```
<210> SEQ ID NO 48
<211> LENGTH: 137
<212> TYPE: PRT
<213> ORGANISM: Artificial Sequence
<220> FEATURE:
<223> OTHER INFORMATION: Synthetic

<400> SEQUENCE: 48
```

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
        115                 120                 125

Leu Met Thr Leu Arg Leu Trp Ser Ser
    130                 135

```
<210> SEQ ID NO 49
```

```
<211> LENGTH: 173
<212> TYPE: PRT
<213> ORGANISM: Artificial Sequence
<220> FEATURE:
<223> OTHER INFORMATION: Synthetic

<400> SEQUENCE: 49

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Cys Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 50
<211> LENGTH: 266
<212> TYPE: PRT
<213> ORGANISM: Artificial Sequence
<220> FEATURE:
<223> OTHER INFORMATION: Synthetic

<400> SEQUENCE: 50

Met Arg Gln Val Ala Arg Val Ile Val Phe Leu Thr Leu Ser Thr Leu
1               5                   10                  15

Ser Leu Ala Lys Thr Thr Gln Pro Ile Ser Met Asp Ser Tyr Glu Gly
            20                  25                  30

Gln Glu Val Asn Ile Thr Cys Ser His Asn Asn Ile Ala Thr Asn Asp
        35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Gly Asp Met Asp Gln
            100                 105                 110

Ala Gly Thr Ala Leu Ile Phe Gly Lys Gly Thr Thr Leu Ser Val Ser
        115                 120                 125

Ser Asp Ile Gln Asn Pro Glu Pro Ala Val Tyr Gln Leu Lys Asp Pro
    130                 135                 140

Arg Ser Gln Asp Ser Thr Leu Cys Leu Phe Thr Asp Phe Asp Ser Gln
```

```
                145                 150                 155                 160
Ile Asn Val Pro Lys Thr Met Glu Ser Gly Thr Phe Ile Thr Asp Lys
                165                 170                 175

Cys Val Leu Asp Met Lys Ala Met Asp Ser Lys Ser Asn Gly Ala Ile
                180                 185                 190

Ala Trp Ser Asn Gln Thr Ser Phe Thr Cys Gln Asp Ile Phe Lys Glu
                195                 200                 205

Thr Asn Ala Thr Tyr Pro Ser Ser Asp Val Pro Cys Asp Ala Thr Leu
                210                 215                 220

Thr Glu Lys Ser Phe Glu Thr Asp Met Asn Leu Asn Phe Gln Asn Leu
225                 230                 235                 240

Leu Val Ile Val Leu Arg Ile Leu Leu Leu Lys Val Ala Gly Phe Asn
                245                 250                 255

Leu Leu Met Thr Leu Arg Leu Trp Ser Ser
                260                 265

<210> SEQ ID NO 51
<211> LENGTH: 306
<212> TYPE: PRT
<213> ORGANISM: Artificial Sequence
<220> FEATURE:
<223> OTHER INFORMATION: Synthetic

<400> SEQUENCE: 51

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
                20                  25                  30

Thr Arg Gly Gln Gln Val Thr Leu Arg Cys Ser Pro Lys Ser Gly His
            35                  40                  45

Asp Thr Val Ser Trp Tyr Gln Gln Ala Leu Gly Gln Gly Pro Gln Phe
        50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
                100                 105                 110

Ser Leu Gly Glu Gly Arg Val Asp Gly Tyr Thr Phe Gly Ser Gly Thr
            115                 120                 125

Arg Leu Thr Val Val Glu Asp Leu Arg Asn Val Thr Pro Pro Lys Val
        130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Cys Thr Asp
                180                 185                 190

Pro Gln Ala Tyr Lys Glu Ser Asn Tyr Ser Tyr Cys Leu Ser Ser Arg
            195                 200                 205

Leu Arg Val Ser Ala Thr Phe Trp His Asn Pro Arg Asn His Phe Arg
        210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
```

245                 250                 255
Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
            275                 280                 285

Ala Val Leu Val Ser Thr Leu Val Val Met Ala Met Val Lys Arg Lys
            290                 295                 300

Asn Ser
305

<210> SEQ ID NO 52
<211> LENGTH: 266
<212> TYPE: PRT
<213> ORGANISM: Artificial Sequence
<220> FEATURE:
<223> OTHER INFORMATION: Synthetic

<400> SEQUENCE: 52

Met Arg Gln Val Ala Arg Val Ile Val Phe Leu Thr Leu Ser Thr Leu
1               5                   10                  15

Ser Leu Ala Lys Thr Thr Gln Pro Ile Ser Met Asp Ser Tyr Glu Gly
            20                  25                  30

Gln Glu Val Asn Ile Thr Cys Ser His Asn Asn Ile Ala Thr Asn Asp
            35                  40                  45

Tyr Ile Thr Trp Tyr Gln Gln Phe Pro Ser Gln Gly Pro Arg Phe Ile
        50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Gly Asp Met Asp Gln
            100                 105                 110

Ala Gly Thr Ala Leu Ile Phe Gly Lys Gly Thr Thr Leu Ser Val Ser
            115                 120                 125

Ser Asp Ile Gln Asn Pro Glu Pro Ala Val Tyr Gln Leu Lys Asp Pro
            130                 135                 140

Arg Ser Gln Asp Ser Thr Leu Cys Leu Phe Thr Asp Phe Asp Ser Gln
145                 150                 155                 160

Ile Asn Val Pro Lys Thr Met Glu Ser Gly Thr Phe Ile Thr Asp Lys
                165                 170                 175

Cys Val Leu Asp Met Lys Ala Met Asp Ser Lys Ser Asn Gly Ala Ile
            180                 185                 190

Ala Trp Ser Asn Gln Thr Ser Phe Thr Cys Gln Asp Ile Phe Lys Glu
            195                 200                 205

Thr Asn Ala Thr Tyr Pro Ser Ser Asp Val Pro Cys Asp Ala Thr Leu
        210                 215                 220

Thr Glu Lys Ser Phe Glu Thr Asp Met Asn Leu Asn Phe Gln Asn Leu
225                 230                 235                 240

Leu Val Ile Val Leu Arg Ile Leu Leu Leu Lys Val Ala Gly Phe Asn
                245                 250                 255

Leu Leu Met Thr Leu Arg Leu Trp Ser Ser
            260                 265

<210> SEQ ID NO 53
<211> LENGTH: 306
<212> TYPE: PRT

<213> ORGANISM: Artificial Sequence
<220> FEATURE:
<223> OTHER INFORMATION: Synthetic

<400> SEQUENCE: 53

```
Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Leu Gly Arg Ala Ser Asn Gln Pro Gln His Phe Gly Asp Gly Thr
        115                 120                 125

Arg Leu Ser Ile Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Cys Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
    290                 295                 300

Asn Ser
305
```

<210> SEQ ID NO 54
<211> LENGTH: 266
<212> TYPE: PRT
<213> ORGANISM: Artificial Sequence
<220> FEATURE:
<223> OTHER INFORMATION: Synthetic

<400> SEQUENCE: 54

```
Met Arg Gln Val Ala Arg Val Ile Val Phe Leu Thr Leu Ser Thr Leu
1               5                   10                  15
```

```
Ser Leu Ala Lys Thr Thr Gln Pro Ile Ser Met Asp Ser Tyr Glu Gly
             20                  25                  30

Gln Glu Val Asn Ile Thr Cys Ser His Asn Asn Ile Ala Thr Asn Asp
         35                  40                  45

Tyr Ile Thr Trp Tyr Gln Gln Phe Pro Ser Gln Gly Pro Arg Phe Ile
     50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                 85                  90                  95

Leu Ser Asp Thr Ala Val Tyr Tyr Cys Leu Val Gly Asp Arg Asp Gln
             100                 105                 110

Ala Gly Thr Ala Leu Ile Phe Gly Lys Gly Thr Thr Leu Ser Val Ser
         115                 120                 125

Ser Asp Ile Gln Asn Pro Glu Pro Ala Val Tyr Gln Leu Lys Asp Pro
     130                 135                 140

Arg Ser Gln Asp Ser Thr Leu Cys Leu Phe Thr Asp Phe Asp Ser Gln
145                 150                 155                 160

Ile Asn Val Pro Lys Thr Met Glu Ser Gly Thr Phe Ile Thr Asp Lys
                 165                 170                 175

Cys Val Leu Asp Met Lys Ala Met Asp Ser Lys Ser Asn Gly Ala Ile
             180                 185                 190

Ala Trp Ser Asn Gln Thr Ser Phe Thr Cys Gln Asp Ile Phe Lys Glu
         195                 200                 205

Thr Asn Ala Thr Tyr Pro Ser Ser Asp Val Pro Cys Asp Ala Thr Leu
     210                 215                 220

Thr Glu Lys Ser Phe Glu Thr Asp Met Asn Leu Asn Phe Gln Asn Leu
225                 230                 235                 240

Leu Val Ile Val Leu Arg Ile Leu Leu Leu Lys Val Ala Gly Phe Asn
                 245                 250                 255

Leu Leu Met Thr Leu Arg Leu Trp Ser Ser
             260                 265

<210> SEQ ID NO 55
<211> LENGTH: 306
<212> TYPE: PRT
<213> ORGANISM: Artificial Sequence
<220> FEATURE:
<223> OTHER INFORMATION: Synthetic

<400> SEQUENCE: 55

Met Gly Pro Gly Leu Cys Trp Ala Leu Leu Cys Leu Leu Gly Ala
1               5                   10                  15

Gly Leu Val Asp Ala Gly Val Thr Gln Ser Pro Thr His Leu Ile Lys
             20                  25                  30

Thr Arg Gly Gln Gln Val Thr Leu Arg Cys Ser Pro Lys Ser Gly His
         35                  40                  45

Asp Thr Val Ser Trp Tyr Gln Gln Ala Leu Gly Gln Gly Pro Gln Phe
     50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                 85                  90                  95

Val Asn Ala Leu Leu Leu Gly Asp Ser Ala Leu Tyr Leu Cys Ala Ser
             100                 105                 110
```

```
Ser Phe Gly Gln Ser Ser Thr Tyr Gly Tyr Thr Phe Gly Ser Gly Thr
            115                 120                 125

Arg Leu Thr Val Val Glu Asp Leu Arg Asn Val Thr Pro Pro Lys Val
130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Cys Thr Asp
                180                 185                 190

Pro Gln Ala Tyr Lys Glu Ser Asn Tyr Ser Tyr Cys Leu Ser Ser Arg
                195                 200                 205

Leu Arg Val Ser Ala Thr Phe Trp His Asn Pro Arg Asn His Phe Arg
210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
                260                 265                 270

Ser Ala Thr Ile Leu Tyr Glu Ile Leu Leu Gly Lys Ala Thr Leu Tyr
                275                 280                 285

Ala Val Leu Val Ser Thr Leu Val Val Met Ala Met Val Lys Arg Lys
                290                 295                 300

Asn Ser
305

<210> SEQ ID NO 56
<211> LENGTH: 269
<212> TYPE: PRT
<213> ORGANISM: Artificial Sequence
<220> FEATURE:
<223> OTHER INFORMATION: Synthetic

<400> SEQUENCE: 56

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
                20                  25                  30

Ser Val Pro Glu Gly Ala Ile Ala Ser Leu Asn Cys Thr Tyr Ser Asp
                35                  40                  45

Arg Gly Ser Gln Ser Phe Phe Trp Tyr Arg Gln Tyr Ser Gly Lys Ser
            50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Ala
                100                 105                 110

Ala Met Asp Ser Ser Tyr Lys Leu Ile Phe Gly Ser Gly Thr Arg Leu
                115                 120                 125

Leu Val Arg Pro Asp Ile Gln Asn Pro Glu Pro Ala Val Tyr Gln Leu
            130                 135                 140

Lys Asp Pro Arg Ser Gln Asp Ser Thr Leu Cys Leu Phe Thr Asp Phe
145                 150                 155                 160
```

```
Asp Ser Gln Ile Asn Val Pro Lys Thr Met Glu Ser Gly Thr Phe Ile
            165                 170                 175

Thr Asp Lys Cys Val Leu Asp Met Lys Ala Met Asp Ser Lys Ser Asn
        180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
        210                 215                 220

Ala Thr Leu Thr Glu Lys Ser Phe Glu Thr Asp Met Asn Leu Asn Phe
225                 230                 235                 240

Gln Asn Leu Leu Val Ile Val Leu Arg Ile Leu Leu Leu Lys Val Ala
                245                 250                 255

Gly Phe Asn Leu Leu Met Thr Leu Arg Leu Trp Ser Ser
                260                 265
```

<210> SEQ ID NO 57
<211> LENGTH: 303
<212> TYPE: PRT
<213> ORGANISM: Artificial Sequence
<220> FEATURE:
<223> OTHER INFORMATION: Synthetic

<400> SEQUENCE: 57

```
Met Gly Thr Arg Leu Phe Phe Tyr Val Ala Leu Cys Leu Leu Trp Ala
1               5                   10                  15

Gly His Arg Asp Ala Gly Ile Thr Gln Ser Pro Arg Tyr Lys Ile Thr
            20                  25                  30

Glu Thr Gly Arg Gln Val Thr Leu Met Cys His Gln Thr Trp Ser His
        35                  40                  45

Ser Tyr Met Phe Trp Tyr Arg Gln Asp Leu Gly His Gly Leu Arg Leu
    50                  55                  60

Ile Tyr Tyr Ser Ala Ala Ala Asp Ile Thr Asp Lys Gly Glu Val Pro
65                  70                  75                  80

Asp Gly Tyr Val Val Ser Arg Ser Lys Thr Glu Asn Phe Pro Leu Thr
                85                  90                  95

Leu Glu Ser Ala Thr Arg Ser Gln Thr Ser Val Tyr Phe Cys Ala Ser
            100                 105                 110

Ser Asp Pro Gly Thr Glu Ala Phe Phe Gly Gln Gly Thr Arg Leu Thr
        115                 120                 125

Val Val Glu Asp Leu Arg Asn Val Thr Pro Pro Lys Val Ser Leu Phe
    130                 135                 140

Glu Pro Ser Lys Ala Glu Ile Ala Asn Lys Gln Lys Ala Thr Leu Val
145                 150                 155                 160

Cys Leu Ala Arg Gly Phe Phe Pro Asp His Val Glu Leu Ser Trp Trp
                165                 170                 175

Val Asn Gly Lys Glu Val His Ser Gly Val Cys Thr Asp Pro Gln Ala
            180                 185                 190

Tyr Lys Glu Ser Asn Tyr Ser Tyr Cys Leu Ser Ser Arg Leu Arg Val
        195                 200                 205

Ser Ala Thr Phe Trp His Asn Pro Arg Asn His Phe Arg Cys Gln Val
    210                 215                 220

Gln Phe His Gly Leu Ser Glu Glu Asp Lys Trp Pro Glu Gly Ser Pro
225                 230                 235                 240

Lys Pro Val Thr Gln Asn Ile Ser Ala Glu Ala Trp Gly Arg Ala Asp
                245                 250                 255
```

```
Cys Gly Ile Thr Ser Ala Ser Tyr Gln Gly Val Leu Ser Ala Thr
            260                 265                 270

Ile Leu Tyr Glu Ile Leu Leu Gly Lys Ala Thr Leu Tyr Ala Val Leu
        275                 280                 285

Val Ser Thr Leu Val Val Met Ala Met Val Lys Arg Lys Asn Ser
    290                 295                 300

<210> SEQ ID NO 58
<211> LENGTH: 27
<212> TYPE: PRT
<213> ORGANISM: Artificial Sequence
<220> FEATURE:
<223> OTHER INFORMATION: Synthetic

<400> SEQUENCE: 58

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

<210> SEQ ID NO 59
<211> LENGTH: 27
<212> TYPE: DNA
<213> ORGANISM: Artificial Sequence
<220> FEATURE:
<223> OTHER INFORMATION: Synthetic

<400> SEQUENCE: 59
gccacagcac tgttgctctt gaagtcc                                         27

<210> SEQ ID NO 60
<211> LENGTH: 24
<212> TYPE: DNA
<213> ORGANISM: Artificial Sequence
<220> FEATURE:
<223> OTHER INFORMATION: Synthetic

<400> SEQUENCE: 60
caggcagtat ctggagtcat tgag                                            24

<210> SEQ ID NO 61
<211> LENGTH: 24
<212> TYPE: PRT
<213> ORGANISM: Artificial Sequence
<220> FEATURE:
<223> OTHER INFORMATION: Synthetic

<400> SEQUENCE: 61

Met Thr Glu Tyr Lys Leu Val Val Val Gly Ala Gly Gly Val Gly Lys
1               5                   10                  15

Ser Ala Leu Thr Ile Gln Leu Ile
            20

<210> SEQ ID NO 62
<211> LENGTH: 24
<212> TYPE: PRT
<213> ORGANISM: Artificial Sequence
<220> FEATURE:
<223> OTHER INFORMATION: Synthetic

<400> SEQUENCE: 62

Met Thr Glu Tyr Lys Leu Val Val Val Gly Ala Asp Gly Val Gly Lys
1               5                   10                  15

Ser Ala Leu Thr Ile Gln Leu Ile
```

```
<210> SEQ ID NO 63
<211> LENGTH: 388
<212> TYPE: DNA
<213> ORGANISM: Homo sapiens

<400> SEQUENCE: 63
atgaggcaag tggcgagagt gatcgtgttc ctgaccctga gtactttgag ccttgctaag      60
accacccagc ccatctccat ggactcatat gaaggacaag aagtgaacat aacctgtagc     120
cacaacaaca ttgctacaaa tgattatatc acgtggtacc aacagtttcc cagccaagga     180
ccacgattta ttattcaagg atacaagaca aaagttacaa cgaagtggc ctccctgttt      240 atccctgccg acagaaagtc cagcactctg agcctgcccc gggtttccct gagcgacact     300
gctgtgtact actgcctcgt gggtgacatg gaccaggcag gaactgctct gatctttggg     360
aagggaacca ccttatcagt gagttcca                                        388

<210> SEQ ID NO 64
<211> LENGTH: 400
<212> TYPE: DNA
<213> ORGANISM: Homo sapiens

<400> SEQUENCE: 64 atgggcccg gctcctctg ctgggcactg ctttgtctcc tgggagcagg cttagtggac        60
gctggagtca cccaaagtcc cacacacctg atcaaaacga gaggacagca agtgactctg     120
agatgctctc ctaagtctgg gcatgacact gtgtcctggt accaacaggc cctgggtcag     180
ggcccccagt ttatctttca gtattatgag gaggaagaga gacagagagg caacttccct     240
gatcgattct caggtcacca gttccctaac tatagctctg agctgaatgt gaacgccttg     300
ttgctggggg actcggccct ctatctctgt gccagcagct gggtgaggg aagagtggac      360 ggctacaccct tcggttcggg gaccaggtta accgttgtag                          400

<210> SEQ ID NO 65
<211> LENGTH: 387
<212> TYPE: DNA
<213> ORGANISM: Artificial Sequence
<220> FEATURE:
<223> OTHER INFORMATION: Synthetic

<400> SEQUENCE: 65
atgcgccagg tggctcgcgt aatcgtgttt ctgactctga gcactctgtc actcgccaag      60
acgacccagc ccatttcaat ggactcatac gaaggtcagg aggtgaatat cacatgctcc     120
cacaataaca ttgctacaaa cgattacatt acatggtatc aacagtttcc ctctcaaggg     180
cctcgattca taatacaagg gtataagacc aaagttacga atgaggtcgc atccctcttt     240
attcccgccg accggaagag ttctactctt tccctgccta gggtgagcct gagtgatact     300
gctgtttact actgcctggt tggagacatg gaccaggcgg aactgccct catattcggc      360 aagggcacga cactctctgt gtcatct                                         387

<210> SEQ ID NO 66
<211> LENGTH: 399
<212> TYPE: DNA
<213> ORGANISM: Artificial Sequence
<220> FEATURE:
<223> OTHER INFORMATION: Synthetic

<400> SEQUENCE: 66
```

```
atgggccag gcctgctttg ctgggcgctg ctgtgcctcc tggtgccgg tttggtggac         60 gctggtgtaa ctcagtcccc aacacatctg atcaagacac gcggccagca ggttacactg        120
cgctgttcac ccaagagtgg gcacgataca gtttcctggt accagcaagc tctgggtcaa        180
ggacctcagt ttatattcca atattacgaa gaggaggagc gccagcgcgg aaatttccca        240
gacagattct ccgggcacca gtttcccaac tactcatctg agctgaacgt taacgccctg        300
ctgctgggag actccgctct ctacctgtgc gcatctagcc tcggggggc tagtaaccag        360 ccccagcact tcggcgacgg aaccaggctg tctattctg                              399

<210> SEQ ID NO 67
<211> LENGTH: 388
<212> TYPE: DNA
<213> ORGANISM: Homo sapiens

<400> SEQUENCE: 67
atgaggcaag tggcgagagt gatcgtgttc ctgaccctga gtactttgag ccttgctaag         60
accacccagc ccatctccat ggactcatat gaaggacaag aagtgaacat aacctgtagc        120
cacaacaaca ttgctacaaa tgattatatc acgtggtacc aacagtttcc cagccaagga        180
ccacgattta ttattcaagg atacaagaca aaagttacaa acgaagtggc ctccctgttt        240
atccctgccg acagaaagtc cagcactctg agcctgcccc gggtttccct gagcgacact        300
gctgtgtact actgcctcgt gggtgacagg gaccaggcag gaactgctct gatctttggg        360
aagggaacca ccttatcagt gagttcca                                           388

<210> SEQ ID NO 68
<211> LENGTH: 400
<212> TYPE: DNA
<213> ORGANISM: Homo sapiens

<400> SEQUENCE: 68
atgggccccg ggctcctctg ctgggcactg ctttgtctcc tgggagcagg cttagtggac         60
gctggagtca cccaaagtcc cacacacctg atcaaaacga gaggacagca agtgactctg        120
agatgctctc ctaagtctgg gcatgacact gtgtcctggt accaacaggc cctgggtcag        180
ggcccccagt ttatctttca gtattatgag gaggaagaga gacagagagg caacttccct        240
gatcgattct caggtcacca gttccctaac tatagctctg agctgaatgt gaacgccttg        300
ttgctggggg actcggccct ctatctctgt gccagcagct tggacagtc aagcacatat        360 ggctacacct tcggttcggg gaccaggtta accgttgtag                              400

<210> SEQ ID NO 69
<211> LENGTH: 397
<212> TYPE: DNA
<213> ORGANISM: Homo sapiens

<400> SEQUENCE: 69
atgaaatcct tgagagtttt actagtgatc ctgtggcttc agttgagctg gtttggagc         60 caacagaagg aggtggagca gaattctgga cccctcagtg ttccagaggg agccattgcc        120
tctctcaact gcacttacag tgaccgaggt tcccagtcct tcttctggta cagacaatat        180
tctgggaaaa gccctgagtt gataatgttc atatactcca atggtgacaa agaagatgga        240
aggtttacag cacagctcaa taagccagc cagtatgttt ctctgctcat cagagactcc        300
cagcccagtg attcagccac ctacctctgt gccgcggcga tggatagcag ctataaattg        360
```

```
atcttcggga gtgggaccag actgctggtc aggcctg                         397

<210> SEQ ID NO 70
<211> LENGTH: 391
<212> TYPE: DNA
<213> ORGANISM: Homo sapiens

<400> SEQUENCE: 70
atgggcacca ggctcttctt ctatgtggcc ctttgtctgc tgtgggcagg acacagggat    60
gctggaatca cccagagccc aagatacaag atcacagaga caggaaggca ggtgaccttg   120
atgtgtcacc agacttggag ccacagctat atgttctggt atcgacaaga cctgggacat   180
gggctgaggc tgatctatta ctcagcagct gctgatatta cagataaagg agaagtcccc   240
gatggctatg ttgtctccag atccaagaca gagaatttcc ccctcactct ggagtcagct   300
acccgctccc agacatctgt gtatttctgc gccagcagtg accccggcac tgaagctttc   360
tttggacaag gcaccagact cacagttgta g                                  391
```

ANTI-KRAS-$^{G12D}$ T CELL RECEPTORS

CROSS-REFERENCE TO RELATED APPLICATIONS

This patent application is a divisional of U.S. application Ser. No. 16/321,899, which is the U.S. national stage of International Application No. PCT/US2017/044615, filed Jul. 31, 2017, which claims the benefit of U.S. Provisional Patent Application No. 62/369,883, filed Aug. 2, 2016, each of which is incorporated by reference in its entirety herein.

STATEMENT REGARDING FEDERALLY SPONSORED RESEARCH AND DEVELOPMENT

This invention was made with Government support under project number ZIABC010984 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 60,918 Byte ASCII (Text) file named "748304_ST25.txt" dated Feb. 26, 2020 Jul. 26, 2017.

BACKGROUND OF THE INVENTION

Some cancers may have very limited treatment options, particularly when the cancer becomes metastatic and unresectable. Despite advances in treatments such as, for example, surgery, chemotherapy, and radiation therapy, the prognosis for many cancers, such as, for example, pancreatic, colorectal, lung, endometrial, ovarian, and prostate cancers, may be poor. Accordingly, there exists an unmet need for additional treatments for cancer.

BRIEF SUMMARY OF THE INVENTION

An embodiment of the invention provides an isolated or purified TCR comprising the amino acid sequences of: (a) SEQ ID NOs: 9-14; (b) SEQ ID NOs: 17-22; (c) SEQ ID NOs: 25-30; or (d) SEQ ID NOs: 33-38.

Another embodiment of the invention provides an isolated or purified polypeptide comprising the amino acid sequences of: (a) SEQ ID NOs: 9-14; (b) SEQ ID NOs: 17-22; (c) SEQ ID NOs: 25-30; or (d) SEQ ID NOs: 33-38.

Another embodiment of the invention provides an isolated or purified protein comprising: (a) a first polypeptide chain comprising the amino acid sequences of SEQ ID NOs: 9-11 and a second polypeptide chain comprising the amino acid sequences of SEQ ID NOs: 12-14; (b) a first polypeptide chain comprising the amino acid sequences of SEQ ID NOs: 17-19 and a second polypeptide chain comprising the amino acid sequences of SEQ ID NOs: 20-22; (c) a first polypeptide chain comprising the amino acid sequences of SEQ ID NOs: 25-27 and a second polypeptide chain comprising the amino acid sequences of SEQ ID NOs: 28-30; or (d) a first polypeptide chain comprising the amino acid sequences of SEQ ID NOs: 33-35 and a second polypeptide chain comprising the amino acid sequences of SEQ ID NOs: 36-38.

The invention further provides related nucleic acids, recombinant expression vectors, host cells, populations of cells, and pharmaceutical compositions relating to the TCRs, polypeptides, and proteins of the invention.

Methods of detecting the presence of cancer in a mammal and methods of treating or preventing cancer in a mammal are further provided by the invention.

BRIEF DESCRIPTION OF THE SEVERAL VIEWS OF THE DRAWING(S)

FIG. 1A is a graph showing IFN-γ production (spots/2e4 cells) as determined by ELISPOT assay of 24 individual TIL cultures after co-culture with autologous dendritic cells transfected with an irrelevant tandem minigene (TMG) RNA (closed circles), or the indicated TMG construct encoding the 61 mutations identified by whole-exomic and transcriptome sequencing (TMG-1 (stars), TMG-2 (Δ), TMG-3 (∇), TMG-4 (open diamond), TMG-5 (closed diamond)).

FIG. 1B is a graph showing IFN-γ production (spots/2e4 cells) as determined by ELISPOT assay (left axis; unshaded bars), and flow cytometric analysis of 4-1BB expression on CD8+ T cells (%) (right axis; shaded bars) of TIL culture #6 after co-culture with dendritic cells (DCs) transfected with an irrelevant TMG RNA or TMG-1, or incubated overnight with the mutated long peptides encoded by TMG-1.

FIG. 1C is a graph showing IFN-γ production as determined by ELISPOT assay (left axis; unshaded bars), and flow cytometric analysis of 4-1BB expression on CD8+ T cells (%) (right axis; shaded bars) of the infusion product (TIL culture #6 after undergoing clinical scale rapid expansion) after co-culture with DCs transfected with the indicated TMG RNA, or incubated overnight with the 24-AA long KRAS-wild type (WT) or KRAS$^{G12D}$ peptides.

FIGS. 2A-2D are graphs showing the results of a TCR-Vβ deep sequencing analysis quantitating the frequency of each of the four identified KRAS$^{G12D}$-reactive T-cell clones in the infusion product (Rx1, filled bar), three metastatic lung samples prior to cell transfer (Tu-1, diamond; Tu-2A, square; and Tu-2B, triangle), the one progressing lesion after cell transfer (Tu-Pro, inverted triangle), and the peripheral blood of the patient before and at various times after cell infusion (circles). Numbers in parentheses indicate the rank of the TCR sequence in the given sample. ⊗ and ND, not detected (<0.0002%). A (TRAV4/TRBV5-6(A)). B (TRAV12-2/TRBV10-2). C (TRAV4/TRBV5-6(B)). D (TRAV4/TRBV5-6 (C)).

FIGS. 3A-3D are graphs showing the expression of the T-cell activation marker 4-1BB on T cells engineered with the TCR comprising the amino acid sequences of SEQ ID NOs: 50 and 51 (TRAV4/TRBV5-6 (A)) (FIG. 3A), SEQ ID NOs: 56 and 57 (TRAV12-2/TRBV10-2) (FIG. 3B), SEQ ID NOs: 54 and 55 (TRAV4/TRBV5-6 (B)) (FIG. 3C), or SEQ ID NOs: 52 and 53 (TRAV4/TRBV5-6 (C)) (FIG. 3D) after overnight coculture with autologous PBMCs incubated with titrating amounts of KRAS wild-type (WT) 9-mer (open circles), G12D mutant KRAS 9mer (closed circles), KRAS WT 10-mer (open triangle), or KRAS G12D mutant KRAS 10-mer peptide (closed triangle).

Figure 4A:
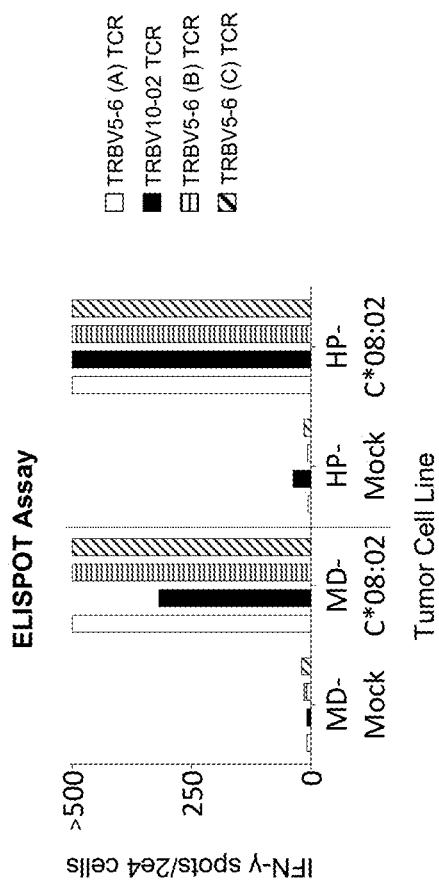
Figure 4B:
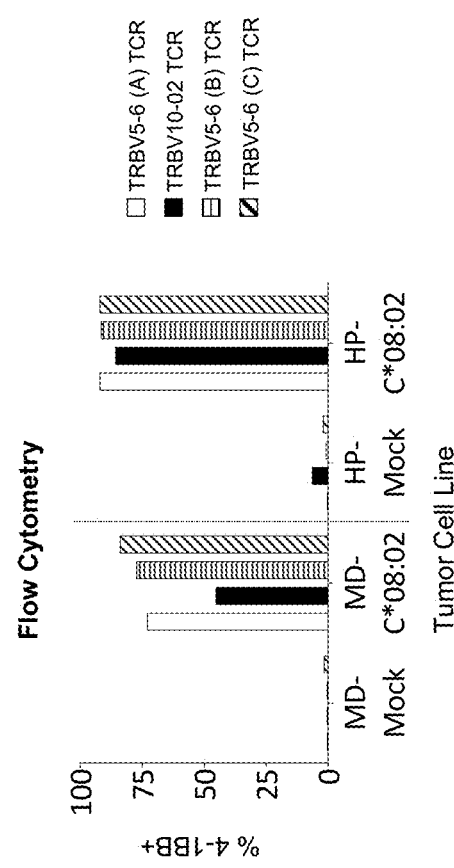

FIGS. 4A and 4B are graphs showing IFN-γ production (spots/2e4 cells) (A) and 4-1BB expression (B) of T cells genetically engineered with the indicated TCR after overnight coculture with two KRAS$^{G12D}$-positive pancreatic cancer cells lines not expressing (Mock) or expressing the HLA-C*08:02 allele. TRBV5-6(A) TCR (unshaded bars); TRBV10-02 TCR (shaded bars); TRBV5-6(B) TCR (horizontal stripes); TRBV5-6(C) TCR (diagonal stripes). MD, MDA-Panc48; HP, HPAC. Flow cytometry data are gated on CD8+ KRAS$^{G12D}$-specific TCR+ cells. ">" greater than ~500 spots not accurate.

FIGS. 5A-5D are graphs showing 4-1BB expression (%) of T cells genetically engineered with the indicated TCR after overnight coculture with target COS cells transduced with full length wild-type (wt) KRAS (unshaded bars) or KRAS-G12D gene (shaded bar) and the indicated HLA allele. TRBV5-6(A) TCR (FIG. 5A); TRBV10-02 TCR (FIG. 5B); TRBV5-6(B) TCR (FIG. 5C); TRBV5-6(C) TCR (FIG. 5D).

DETAILED DESCRIPTION OF THE INVENTION

Kirsten rat sarcoma viral oncogene homolog (KRAS), also referred to as GTPase KRas, V-Ki-Ras2 Kirsten rat sarcoma viral oncogene, or KRAS2, is a member of the small GTPase superfamily. There are two transcript variants of KRAS: KRAS variant A and KRAS variant B. Hereinafter, references to "KRAS" (mutated or unmutated) refer to both variant A and variant B, unless specified otherwise. Without being bound to a particular theory or mechanism, it is believed that, when mutated, KRAS may be involved in signal transduction early in the oncogenesis of many human cancers. A single amino acid substitution may activate the protein. When activated, mutated KRAS binds to guanosine-5'-triphosphate (GTP) and converts GTP to guanosine 5'-diphosphate (GDP). The mutated KRAS protein product may be constitutively activated. Mutated KRAS protein may be expressed in any of a variety of human cancers such as, for example, pancreatic (e.g., pancreatic carcinoma), colorectal, lung (e.g., lung adenocarcinoma), endometrial, ovarian (e.g., epithelial ovarian cancer), and prostate cancers.

An embodiment of the invention provides an isolated or purified TCR having antigenic specificity for mutated human KRAS (hereinafter, "mutated KRAS"). Hereinafter, references to a "TCR" also refer to functional portions and functional variants of the TCR, unless specified otherwise. The inventive TCR may have antigenic specificity for any KRAS (protein, polypeptide or peptide) with a G12D mutation.

In an embodiment of the invention, the TCR has antigenic specificity for a KRAS protein with the G12D mutation, the KRAS protein comprising or consisting of the amino acid sequence of SEQ ID NO: 3 or 4. The mutated KRAS variant A protein amino acid sequence of SEQ ID NO: 3 generally corresponds to positions 1-189 of the unmutated, wild-type (WT) KRAS protein variant A amino acid sequence of SEQ ID NO: 1 with the exception that in SEQ ID NO: 3, the glycine at position 12 is substituted with aspartic acid. The mutated KRAS variant B protein amino acid sequence of SEQ ID NO: 4 generally corresponds to positions 1-188 of the unmutated, WT KRAS protein variant B amino acid sequence of SEQ ID NO: 2 with the exception that in SEQ ID NO: 4, the glycine at position 12 is substituted with aspartic acid.

In an embodiment of the invention, the TCR has antigenic specificity for a KRAS peptide with the G12D mutation described above, the KRAS peptide having any length. For example, the TCR may have antigenic specificity for a KRAS peptide with the G12D mutation, the KRAS peptide having a length of about 8 to about 24 amino acid residues, preferably about 9 to about 11 amino acid residues. In an embodiment of the invention, the TCR may have antigenic specificity for a KRAS peptide with the G12D mutation, the KRAS peptide having a length of about 8 amino acid residues, about 9 amino acid residues, about 10 amino acid residues, about 11 amino acid residues, about 12 amino acid residues, or about 24 amino acid residues. For example, the TCR may have antigenic specificity for a KRAS$_{10-18}$ peptide with the G12D mutation, the peptide comprising or consisting of the amino acid sequence of GADGVGKSA (SEQ ID NO: 8). The mutated KRAS peptide amino acid sequence of SEQ ID NO: 8 with the G12D mutation generally corresponds to positions 1-9 of the unmutated, WT KRAS$_{10-18}$ peptide amino acid sequence of SEQ ID NO: 7 with the exception that in SEQ ID NO: 8, the glycine at position 3 is substituted with aspartic acid.

In still another embodiment of the invention, the TCR may have antigenic specificity for a KRAS peptide with the G12D mutation, the mutated KRAS peptide comprising or consisting of the amino acid sequence of GADGVGKSA (mutated KRAS$_{10-18}$; SEQ ID NO: 8) or GADGVGKSAL (mutated KRAS$_{10-19}$; SEQ ID NO: 6). In an exemplary embodiment, the TCR has antigenic specificity for a mutated KRAS epitope, the mutated KRAS epitope comprising or consisting of the amino acid sequence of GADGVGKSA (mutated KRAS$_{10-18}$; SEQ ID NO: 8) or GADGVGKSAL (mutated KRAS$_{10-19}$; SEQ ID NO: 6).

In an embodiment of the invention, the inventive TCRs are able to recognize mutated KRAS within the context of an HLA-Cw8 molecule. In this regard, the TCR may elicit an immune response upon binding to mutated KRAS within the context of an HLA-Cw8 molecule. The inventive TCRs are able to recognize mutated KRAS that is presented by an HLA-Cw8 molecule and may bind to the HLA-Cw8 molecule in addition to mutated KRAS. Exemplary HLA-Cw8 molecules, in the context of which the inventive TCRs recognize mutated KRAS, include those encoded by the HLA-Cw*0801, HLA-Cw*0802, HLA-Cw*0803, HLA-Cw*0804, HLA-Cw*0805, HLA-Cw*0806, HLA-Cw*0807, HLA-Cw*0808, and HLA-Cw*0809 alleles. In a preferred embodiment, the TCRs recognize mutated KRAS within the context of an HLA-Cw*0802 molecule.

In an embodiment of the invention, in addition to having the ability to recognize mutated KRAS within the context of an HLA-Cw8 molecule, one of the inventive TCRs (TRAV12-2/TRBV10-2 (Table 5)) is also able to recognize mutated KRAS within the context of an HLA-Cw5 molecule. In this regard, the TCR may elicit an immune response upon binding to mutated KRAS within the context of an HLA-Cw5 molecule. The inventive TCR is able to recognize mutated KRAS that is presented by an HLA-Cw5 molecule and may bind to the HLA-Cw5 molecule in addition to mutated KRAS. Exemplary HLA-Cw5 molecules, in the context of which the inventive TCR recognizes mutated KRAS, include those encoded by the HLA-Cw*0501, HLA-Cw*0502, HLA-Cw*0503, HLA-Cw*0504, HLA-Cw*0505, HLA-Cw*0506, HLA-HLA-Cw*0508, HLA-Cw*0509, and HLA-Cw*0510 alleles. In a preferred embodiment, the TCR recognizes mutated KRAS within the context of an HLA-Cw*0501 molecule. The amino acid sequences of HLA-Cw*0802 and HLA-Cw*0501 differ from one another by only two amino acid residues. Without being bound to a particular theory or mechanism, it is believed that the TRAV12-2/TRBV10-2 TCR may also recognize mutated KRAS that is presented by other HLA molecules that are similar to one or both of HLA-Cw*0802 and HLA-Cw*0501.

The TCRs of the invention provide many advantages, including when expressed by cells used for adoptive cell transfer. Mutated KRAS is expressed by cancer cells and is not expressed by normal, noncancerous cells. Without being bound to a particular theory or mechanism, it is believed that the inventive TCRs advantageously target the destruction of cancer cells while minimizing or eliminating the destruction of normal, non-cancerous cells, thereby reducing, for example, by minimizing or eliminating, toxicity. Moreover, the inventive TCRs may, advantageously, successfully treat or prevent mutated KRAS-positive cancers that do not respond to other types of treatment such as, for example, chemotherapy, surgery, or radiation. Additionally, the inventive TCRs may provide highly avid recognition of mutated KRAS, which may provide the ability to recognize unmanipulated tumor cells (e.g., tumor cells that have not been treated with interferon (IFN)-γ, transfected with a vector encoding one or both of mutated KRAS and HLA-Cw*0802, pulsed with a KRAS peptide with the G12D mutation, or a combination thereof). Moreover, the HLA-Cw*0802 allele is expressed in up to about 8% and about 11% of American Caucasian and African American ethnicities, respectively. Accordingly, the inventive TCRs may increase the number of immunotherapy-eligible cancer patients to include those patients that express the HLA-Cw*0802 allele who may not be eligible for immunotherapy using TCRs that recognize antigen in the context of other MHC molecules.

The phrase "antigenic specificity," as used herein, means that the TCR can specifically bind to and immunologically recognize mutated KRAS with high avidity. For example, a TCR may be considered to have "antigenic specificity" for mutated KRAS if about $1 \times 10^4$ to about $1 \times 10^5$ T cells expressing the TCR secrete at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, 20,000 pg/mL or more, or a range defined by any two of the foregoing values) of IFN-γ upon co-culture with (a) antigen-negative HLA-Cw*0802$^+$ target cells pulsed with a low concentration of mutated KRAS peptide (e.g., about 0.05 ng/mL to about 10 ng/mL, 1 ng/mL, 2 ng/mL, 5 ng/mL, 8 ng/mL, 10 ng/mL, or a range defined by any two of the foregoing values) or (b) antigen-negative HLA-Cw*0802$^+$ target cells into which a nucleotide sequence encoding mutated KRAS has been introduced such that the target cell expresses mutated KRAS. Cells expressing the inventive TCRs may also secrete IFN-γ upon co-culture with antigen-negative HLA-Cw*0802$^+$ target cells pulsed with higher concentrations of mutated KRAS peptide.

Alternatively or additionally, a TCR may be considered to have "antigenic specificity" for mutated KRAS if T cells expressing the TCR secrete at least twice as much IFN-γ upon co-culture with (a) antigen-negative HLA-Cw*0802$^+$ target cells pulsed with a low concentration of mutated KRAS peptide or (b) antigen-negative HLA-Cw*0802$^+$ target cells into which a nucleotide sequence encoding mutated KRAS has been introduced such that the target cell expresses mutated KRAS as compared to the amount of IFN-γ expressed by a negative control. The negative control may be, for example, (i) T cells expressing the TCR, co-cultured with (a) antigen-negative HLA-Cw*0802$^+$ target cells pulsed with the same concentration of an irrelevant peptide (e.g., some other peptide with a different sequence from the mutated KRAS peptide) or (b) antigen-negative HLA-Cw*0802$^+$ target cells into which a nucleotide sequence encoding an irrelevant peptide has been introduced such that the target cell expresses the irrelevant peptide, or (ii) untransduced T cells (e.g., derived from PBMC, which do not express the TCR) co-cultured with (a) antigen-negative HLA-Cw*0802$^+$ target cells pulsed with the same concentration of mutated KRAS peptide or (b) antigen-negative HLA-Cw*0802$^+$ target cells into which a nucleotide sequence encoding mutated KRAS has been introduced such that the target cell expresses mutated KRAS. IFN-γ secretion may be measured by methods known in the art such as, for example, enzyme-linked immunosorbent assay (ELISA).

Alternatively or additionally, a TCR may be considered to have "antigenic specificity" for mutated KRAS if at least twice as many of the numbers of T cells expressing the TCR secrete IFN-γ upon co-culture with (a) antigen-negative HLA-Cw*0802$^+$ target cells pulsed with a low concentration of mutated KRAS peptide or (b) antigen-negative HLA-Cw*0802$^+$ target cells into which a nucleotide sequence encoding mutated KRAS has been introduced such that the target cell expresses mutated KRAS as compared to the numbers of negative control T cells that secrete IFN-γ. The concentration of peptide and the negative control may be as described herein with respect to other aspects of the invention. The numbers of cells secreting IFN-γ may be measured by methods known in the art such as, for example, ELISPOT.

Alternatively or additionally, a TCR may be considered to have "antigenic specificity" for mutated KRAS if T cells expressing the TCR upregulate expression of one or more T-cell activation markers as measured by, for example, flow cytometry after stimulation with target cells expressing mutated KRAS. Examples of T-cell activation markers include 4-1BB, OX40, CD107a, CD69, and cytokines that are upregulated upon antigen stimulation (e.g., tumor necrosis factor (TNF), interleukin (IL)-2, etc.).

The invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for mutated KRAS.

In an embodiment of the invention, the TCR comprises two polypeptide chains, each of which comprises a variable region comprising a complementarity determining region (CDR)1, a CDR2, and a CDR3 of a TCR. In an embodiment of the invention, the TCR comprises a first polypeptide chain comprising a CDR1 comprising the amino acid sequence of SEQ ID NO: 9 (CDR1 of α chain), a CDR2 comprising the amino acid sequence of SEQ ID NO: 10 (CDR2 of α chain), and a CDR3 comprising the amino acid sequence of SEQ ID NO: 11 (CDR3 of α chain), and a second polypeptide chain comprising a CDR1 comprising the amino acid sequence of SEQ ID NO: 12 (CDR1 of β chain), a CDR2 comprising the amino acid sequence of SEQ ID NO: 13 (CDR2 of β chain), and a CDR3 comprising the amino acid sequence of SEQ ID NO: 14 (CDR3 of β chain).

In another embodiment of the invention, the TCR comprises a first polypeptide chain comprising a CDR1 comprising the amino acid sequence of SEQ ID NO: 17 (CDR1 of α chain), a CDR2 comprising the amino acid sequence of SEQ ID NO: 18 (CDR2 of α chain), and a CDR3 comprising the amino acid sequence of SEQ ID NO: 19 (CDR3 of α chain), and a second polypeptide chain comprising a CDR1 comprising the amino acid sequence of SEQ ID NO: 20 (CDR1 of β chain), a CDR2 comprising the amino acid sequence of SEQ ID NO: 21 (CDR2 of β chain), and a CDR3 comprising the amino acid sequence of SEQ ID NO: 22 (CDR3 of β chain).

In another embodiment of the invention, the TCR comprises a first polypeptide chain comprising a CDR1 comprising the amino acid sequence of SEQ ID NO: 25 (CDR1 of α chain), a CDR2 comprising the amino acid sequence of SEQ ID NO: 26 (CDR2 of α chain), and a CDR3 comprising the amino acid sequence of SEQ ID NO: 27 (CDR3 of α chain), and a second polypeptide chain comprising a CDR1 comprising the amino acid sequence of SEQ ID NO: 28 (CDR1 of β chain), a CDR2 comprising the amino acid sequence of SEQ ID NO: 29 (CDR2 of β chain), and a CDR3 comprising the amino acid sequence of SEQ ID NO: 30 (CDR3 of β chain).

In another embodiment of the invention, the TCR comprises a first polypeptide chain comprising a CDR1 comprising the amino acid sequence of SEQ ID NO: 33 (CDR1 of α chain), a CDR2 comprising the amino acid sequence of SEQ ID NO: 34 (CDR2 of α chain), and a CDR3 comprising the amino acid sequence of SEQ ID NO: 35 (CDR3 of α chain), and a second polypeptide chain comprising a CDR1 comprising the amino acid sequence of SEQ ID NO: 36 (CDR1 of β chain), a CDR2 comprising the amino acid sequence of SEQ ID NO: 37 (CDR2 of β chain), and a CDR3 comprising the amino acid sequence of SEQ ID NO: 38 (CDR3 of β chain).

In this regard, the inventive TCR can comprise any one or more of the amino acid sequences selected from the group consisting of SEQ ID NOs: 9-14, 17-22, 25-30, and 33-38. In an embodiment of the invention, the TCR comprises the amino acid sequences of: (i) SEQ ID NO: 9-11; (ii); SEQ ID NOs: 12-14; (iii) SEQ ID NOs: 17-19; (iv) SEQ ID NOs: 20-22; (v) SEQ ID NOs: 25-27; (vi) SEQ ID NOs: 28-30; (vii) SEQ ID NOs: 33-35; or (viii) SEQ ID NOs: 36-38. In an especially preferred embodiment, the TCR comprises the amino acid sequences of: (a) all of SEQ ID NOs: 9-14; (b) all of SEQ ID NOs: 17-22; (c) all of SEQ ID NOs: 25-30; or (d) all of SEQ ID NOs: 33-38.

In an embodiment of the invention, the TCR comprises an amino acid sequence of a variable region of a TCR comprising the CDRs set forth above. In this regard, the TCR can comprise the amino acid sequence of: SEQ ID NO: 15 (variable region of α chain); SEQ ID NO: 23 (variable region of α chain); SEQ ID NO: 31 (variable region of α chain); SEQ ID NO: 39 (variable region of α chain); SEQ ID NO: 16 (variable region of β chain); SEQ ID NO: 24 (variable region of β chain); SEQ ID NO: 32 (variable region of β chain); SEQ ID NO: 40 (variable region of β chain); both SEQ ID NOs: 15 and 16; both SEQ ID NOs: 23 and 24; both SEQ ID NOs: 31 and 32; or both SEQ ID NOs: 39 and 40. Preferably, the inventive TCR comprises the amino acid sequences of (i) both of SEQ ID NOs: 15-16; (ii) both of SEQ ID NOs: 23-24; (iii) both of SEQ ID NOs: 31-32; or (iv) both of SEQ ID NOs: 39-40.

The inventive TCRs may further comprise an α chain constant region and a β chain constant region. The constant region may be derived from any suitable species such as, e.g., human or mouse. In an embodiment of the invention, the TCRs further comprise a murine α and β chain constant regions or human α and β chain constant regions. As used herein, the term "murine" or "human," when referring to a TCR or any component of a TCR described herein (e.g., complementarity determining region (CDR), variable region, constant region, α chain, and/or β chain), means a TCR (or component thereof) which is derived from a mouse or a human, respectively, i.e., a TCR (or component thereof) that originated from or was, at one time, expressed by a mouse T cell or a human T cell, respectively.

In an embodiment of the invention, the TCRs further comprise human α and β chain constant regions. In this regard, the TCR can comprise the amino acid sequence of SEQ ID NO: 41, wherein X at position 1 is any naturally occurring amino acid residue (the constant region of a human α chain), SEQ ID NO: 42 (the constant region of a human β chain), SEQ ID NO: 43 (the constant region of a human β chain), both SEQ ID NOs: 41 and 42, or both SEQ ID NOs: 41 and 43. In an embodiment of the invention, the TCR comprises any of the human constant regions described herein in combination with any of the CDR regions described herein. In this regard, the TCR may comprise the amino acid sequences of: (a) all of SEQ ID NOs: 9-14, 41, and 42; (b) all of SEQ ID NOs: 17-22, 41, and 42; (c) all of SEQ ID NOs: 25-30, 41, and 42; (d) all of SEQ ID NOs: 33-38, 41, and 42; (e) all of SEQ ID NOs: 9-14, 41, and 43; (f) all of SEQ ID NOs: 17-22, 41, and 43; (g) all of SEQ ID NOs: 25-30, 41, and 43; or (h) all of SEQ ID NOs: 33-38, 41, and 43. In an embodiment of the invention, the TCR comprises any of the human constant regions described herein in combination with any of the variable regions described herein. In this regard, the TCR may comprise the amino acid sequences of: (i) all of SEQ ID NOs: 15-16, 41, and 42; (ii) all of SEQ ID NOs: 23-24, 41, and 42; (iii) all of SEQ ID NOs: 31-32, 41, and 42; (iv) all of SEQ ID NOs: 39-42; (v) all of SEQ ID NOs: 15-16, 41, and 43; (vi) all of SEQ ID NOs: 23-24, 41, and 43; (vii) all of SEQ ID NOs: 31-32, 41, and 43; or (viii) all of SEQ ID NOs: 39-40, 41, and 43.

An embodiment of the invention provides a chimeric TCR comprising a human variable region and a murine constant region, wherein the TCR has antigenic specificity for mutated KRAS presented in the context of an HLA-Cw8 molecule. The murine constant region may provide any one or more advantages. For example, the murine constant region may diminish mispairing of the inventive TCR with the endogenous TCRs of the host cell into which the inventive TCR is introduced. Alternatively or additionally, the murine constant region may increase expression of the inventive TCR as compared to the same TCR with a human constant region. The chimeric TCR may comprise the amino acid sequence of SEQ ID NO: 44 (wild-type (WT) murine α chain constant region), SEQ ID NO: 45 (WT murine β chain constant region), or both SEQ ID NOs: 44 and 45. Preferably, the inventive TCR comprises the amino acid sequences of both SEQ ID NOs: 44 and 45. The chimeric TCR may comprise any of the murine constant regions described herein in combination with any of the CDR regions as described herein with respect to other aspects of the invention. In this regard, the TCR may comprise the amino acid sequences of: (a) all of SEQ ID NOs: 9-14, 44, and 45; (b) all of SEQ ID NOs: 17-22, 44, and 45; (c) all of SEQ ID NOs: 25-30, 44, and 45; or (d) all of SEQ ID NOs: 33-38, 44, and 45. In another embodiment of the invention, the chimeric TCR may comprise any of the murine constant regions described herein in combination with any of the variable regions described herein with respect to other aspects of the invention. In this regard, the TCR may comprise the amino acid sequences of: (i) SEQ ID NOs: 15-16, 44, and 45; (ii) SEQ ID NOs: 23-24, 44, and 45; (iii) SEQ ID NOs: 31-32, 44, and 45; or (iv) SEQ ID NOs: 39-40, 44, and 45;

In an embodiment of the invention, the TCR comprises a substituted constant region. In this regard, the TCR may comprise the amino acid sequence of any of the TCRs described herein with one, two, three, or four amino acid substitution(s) in the constant region of one or both of the α and β chain. Preferably, the TCR comprises a murine constant region with one, two, three, or four amino acid substitution(s) in the murine constant region of one or both of the α and β chains. In an especially preferred embodiment, the TCR comprises a murine constant region with one, two, three, or four amino acid substitution(s) in the murine constant region of the α chain and one amino acid substitution in the murine constant region of the β chain. In some embodiments, the TCRs comprising the substituted constant region advantageously provide one or more of increased recognition of mutated KRAS+ targets, increased expression by a host cell, diminished mispairing with endogenous TCRs, and increased anti-tumor activity as compared to the parent TCR comprising an unsubstituted (wild-type) constant region. In general, the substituted amino acid sequences of the murine constant regions of the TCR α and β chains, SEQ ID NOs: 46 and 47, respectively, correspond with all or portions of the unsubstituted murine constant region amino acid sequences SEQ ID NOs: 44 and 45, respectively, with SEQ ID NO: 46 having one, two, three, or four amino acid substitution(s) when compared to SEQ ID NO: 44 and SEQ ID NO: 47 having one amino acid substitution when compared to SEQ ID NO: 45. In this regard, an embodiment of the invention provides a TCR comprising the amino acid sequences of (a) SEQ ID NO: 46 (constant region of α chain), wherein (i) X at position 48 is Thr or Cys; (ii) X at position 112 is Ser, Ala, Val, Leu, Ile, Pro, Phe, Met, or Trp; (iii) X at position 114 is Met, Ala, Val, Leu, Ile, Pro, Phe, or Trp; and (iv) X at position 115 is Gly, Ala, Val, Leu, Ile, Pro, Phe, Met, or Trp; and (b) SEQ ID NO: 47 (constant region of β chain), wherein X at position 57 is Ser or Cys. In an embodiment of the invention, the TCR comprising SEQ ID NO: 46 does not comprise SEQ ID NO: 44 (unsubstituted murine constant region of α chain). In an embodiment of the invention, the TCR comprising SEQ ID NO: 47 does not comprise SEQ ID NO: 45 (unsubstituted murine constant region of β chain).

In an embodiment of the invention, the substituted constant region includes cysteine substitutions in the constant region of one or both of the α and β chains to provide a cysteine-substituted TCR. Opposing cysteines in the α and the β chains provide a disulfide bond that links the constant regions of the α and the β chains of the substituted TCR to one another and which is not present in a TCR comprising the unsubstituted murine constant regions. In this regard, the TCR may be a cysteine-substituted TCR in which one or both of the native Thr at position 48 (Thr48) of SEQ ID NO: 44 and the native Ser at position 57 (Ser57) of SEQ ID NO: 45 may be substituted with Cys. Preferably, both of the native Thr48 of SEQ ID NO: 44 and the native Ser57 of SEQ ID NO: 45 are substituted with Cys. In an embodiment, the cysteine-substituted TCR comprises an α chain constant region comprising the amino acid sequence of SEQ ID NO: 46, wherein X at position 48 is Cys, X at position 112 is the native Ser, X at position 114 is the native Met, and X at position 115 is the native Gly, and a β chain constant region comprising the amino acid sequence of SEQ ID NO: 47, wherein X at position 57 is Cys. The cysteine-substituted TCRs of the invention may include the substituted constant region in addition to any of the CDRs or variable regions described herein.

In an embodiment of the invention, the substituted amino acid sequence includes substitutions of one, two, or three amino acids in the transmembrane (TM) domain of the constant region of one or both of the α and β chains with a hydrophobic amino acid to provide a hydrophobic amino acid-substituted TCR. The hydrophobic amino acid substitution(s) in the TM domain of the TCR may increase the hydrophobicity of the TM domain of the TCR as compared to a TCR that lacks the hydrophobic amino acid substitution(s) in the TM domain. In this regard, the TCR is a hydrophobic amino acid-substituted TCR in which one, two, or three of the native Ser112, Met114, and Gly115 of SEQ ID NO: 44 may, independently, be substituted with Ala, Val, Leu, Ile, Pro, Phe, Met, or Trp; preferably with Leu, Ile, or Val. Preferably, all three of the native Ser112, Met114, and Gly115 of SEQ ID NO: 44 may, independently, be substituted with Ala, Val, Leu, Ile, Pro, Phe, Met, or Trp; preferably with Leu, Ile, or Val. In an embodiment, the hydrophobic amino acid-substituted TCR comprises an α chain constant region comprising the amino acid sequence of SEQ ID NO: 46, wherein X at position 48 is the native Thr, X at position 112 is Ser, Ala, Val, Leu, Ile, Pro, Phe, Met, or Trp, X at position 114 is Met, Ala, Val, Leu, Ile, Pro, Phe, or Trp, and X at position 115 is Gly, Ala, Val, Leu, Ile, Pro, Phe, Met, or Trp, and a β chain constant region comprising the amino acid sequence of SEQ ID NO: 47, wherein X at position 57 is the native Ser, wherein the hydrophobic amino acid-substituted TCR comprising SEQ ID NO: 46 does not comprise SEQ ID NO: 44 (unsubstituted murine constant region of α chain). In a preferred embodiment, the hydrophobic amino acid-substituted TCR comprises an α chain constant region comprising the amino acid sequence of SEQ ID NO: 46, wherein X at position 48 is the native Thr, X at position 112 is Leu, X at position 114 is Ile, and X at position 115 is Val, and a β chain constant region comprising the amino acid sequence of SEQ ID NO: 47, wherein X at position 57 is the native Ser. The hydrophobic amino acid-substituted TCRs of the invention may include the substituted constant region in addition to any of the CDRs or variable regions described herein.

In an embodiment of the invention, the substituted amino acid sequence includes the cysteine substitutions in the constant region of one or both of the α and β chains in combination with the substitution(s) of one, two, or three amino acids in the transmembrane (TM) domain of the constant region of one or both of the α and β chains with a hydrophobic amino acid (also referred to herein as "cysteine-substituted, hydrophobic amino acid-substituted TCR"). In this regard, the TCR is a cysteine-substituted, hydrophobic amino acid-substituted TCR in which the native Thr48 of SEQ ID NO: 46 is substituted with Cys; one, two, or three of the native Ser112, Met114, and Gly115 of SEQ ID NO: 46 are, independently, substituted with Ala, Val, Leu, Ile, Pro, Phe, Met, or Trp; preferably with Leu, Ile, or Val; and the native Ser57 of SEQ ID NO: 47 is substituted with Cys. Preferably, all three of the native Ser112, Met114, and Gly115 of SEQ ID NO: 46 may, independently, be substituted with Ala, Val, Leu, Ile, Pro, Phe, Met, or Trp; preferably with Leu, Ile, or Val. In an embodiment, the cysteine-substituted, hydrophobic amino acid-substituted TCR comprises an α chain comprising the amino acid sequence of SEQ ID NO: 46, wherein X at position 48 is Cys, X at position 112 is Ser, Ala, Val, Leu, Ile, Pro, Phe, Met, or Trp, X at position 114 is Met, Ala, Val, Leu, Ile, Pro, Phe, or Trp, and X at position 115 is Gly, Ala, Val, Leu, Ile, Pro, Phe, Met, or Trp, and a β chain comprising the amino acid sequence of SEQ ID NO: 47, wherein X at position 57 is Cys, wherein SEQ ID NO: 46 does not comprise SEQ ID NO: 44 (unsubstituted α chain) and SEQ ID NO: 47 does not comprise SEQ ID NO: 45 (unsubstituted β chain). Preferably, the cysteine-substituted, hydrophobic amino acid-substituted TCR comprises an α chain comprising the amino acid sequence of SEQ ID NO: 46, wherein X at position 48 is Cys, X at position 112 is Leu, X at position 114 is Ile, X at position 115 is Val, and a β chain comprising the amino acid sequence of SEQ ID NO: 47, wherein X at position 57 is Cys. In this regard, the cysteine-substituted, hydrophobic amino acid-substituted TCR comprises an α chain constant region comprising the amino acid sequence of SEQ ID NO: 48 and a β chain constant region comprising the amino acid sequence of SEQ ID NO: 49. The cysteine-substituted, hydrophobic amino acid-substituted TCRs of the invention may include the substituted constant region in addition to any of the CDRs or variable regions described herein.

In an embodiment of the invention, the inventive cysteine-substituted, hydrophobic amino acid-substituted TCR can comprise an α chain of a TCR and a β chain of a TCR. Each of the α chain and β chain of the inventive TCR can independently comprise any amino acid sequence. In this regard, the α chain of the inventive TCR can comprise the amino acid sequence of SEQ ID NO: 50, 52, 54, or 56. An α chain of this type can be paired with any β chain of a TCR. In this regard, the α chain of the inventive TCR can comprise the amino acid sequence of SEQ ID NO: 51, 53, 55, or 57. The inventive TCR, therefore, can comprise the amino acid sequence of SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, both SEQ ID NOs: 50 and 51, both SEQ ID NOs: 52 and 53, both SEQ ID NO: 54 and 55, or both SEQ ID NOs: 56 and 57. Preferably, the inventive TCR comprises the amino acid sequences of (1) both of SEQ ID NOs: 50-51; (2) both of SEQ ID NOs: 52-53; (3) both of SEQ ID NOs: 54-55; or (4) both of SEQ ID NOs: 56-57.

Also provided by the invention is a polypeptide comprising a functional portion of any of the TCRs described herein. The term "polypeptide," as used herein, includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to mutated KRAS. The term "functional portion," when used in reference to a TCR, refers to any part or fragment of the TCR of the invention, which part or fragment retains the biological activity of the TCR of which it is a part (the parent TCR). Functional portions encompass, for example, those parts of a TCR that retain the ability to specifically bind to mutated KRAS (e.g., within the context of an HLA-Cw*0802 molecule), or detect, treat, or prevent cancer, to a similar extent, the same extent, or to a higher extent, as the parent TCR. In reference to the parent TCR, the functional portion can comprise, for instance, about 10%, 25%, 30%, 50%, 68%, 80%, 90%, 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to mutated KRAS; and/or having the ability to detect cancer, treat or prevent cancer, etc. More desirably, the additional amino acids enhance the biological activity, as compared to the biological activity of the parent TCR.

The polypeptide can comprise a functional portion of either or both of the α and β chains of the TCRs of the invention, such as a functional portion comprising one or more of the CDR1, CDR2, and CDR3 of the variable region(s) of the α chain and/or β chain of a TCR of the invention. In an embodiment of the invention, the polypeptide can comprise the amino acid sequence of SEQ ID NO: 9 (CDR1 of α chain), SEQ ID NO: 10 (CDR2 of α chain), SEQ ID NO: 11 (CDR3 of α chain), SEQ ID NO: 12 (CDR1 of β chain), SEQ ID NO: 13 (CDR2 of β chain), SEQ ID NO: 14 (CDR3 of β chain), or a combination thereof. In another embodiment of the invention, the polypeptide can comprise the amino acid sequence of SEQ ID NO: 17 (CDR1 of α chain), SEQ ID NO: 18 (CDR2 of α chain), SEQ ID NO: 19 (CDR3 of α chain), SEQ ID NO: 20 (CDR1 of β chain), SEQ ID NO: 21 (CDR2 of β chain), SEQ ID NO: 22 (CDR3 of β chain), or a combination thereof. In another embodiment of the invention, the polypeptide can comprise the amino acid sequence of SEQ ID NO: 25 (CDR1 of α chain), SEQ ID NO: 26 (CDR2 of α chain), SEQ ID NO: 27 (CDR3 of α chain), SEQ ID NO: 28 (CDR1 of β chain), SEQ ID NO: 29 (CDR2 of β chain), SEQ ID NO: 30 (CDR3 of β chain), or a combination thereof. In another embodiment of the invention, the polypeptide can comprise the amino acid sequence of SEQ ID NO: 33 (CDR1 of α chain), SEQ ID NO: 34 (CDR2 of α chain), SEQ ID NO: 35 (CDR3 of α chain), SEQ ID NO: 36 (CDR1 of β chain), SEQ ID NO: 37 (CDR2 of β chain), SEQ ID NO: 38 (CDR3 of β chain), or a combination thereof. Preferably, the polypeptide comprises the amino acid sequences of (a) both of SEQ ID NOs: 9-14; (b) both of SEQ ID NOs: 17-22; (c) both of SEQ ID NOs: 25-30; or (d) both of SEQ ID NOs: 33-38.

In an embodiment of the invention, the inventive polypeptide can comprise, for instance, the variable region of the inventive TCR comprising a combination of the CDR regions set forth above. In this regard, the polypeptide can comprise the amino acid sequence of SEQ ID NO: 15 (variable region of α chain), SEQ ID NO: 16 (variable region of β chain), both SEQ ID NOs: 15 and 16, SEQ ID NO: 23 (variable region of α chain), SEQ ID NO: 24 (variable region of β chain), both SEQ ID NOs: 23 and 24, SEQ ID NO: 31 (variable region of α chain), SEQ ID NO: 32 (variable region of β chain), both SEQ ID NOs: 31 and 32, SEQ ID NO: 39 (variable region of α chain), SEQ ID NO: 40 (variable region of β chain), or both SEQ ID NOs: 39 and 40. Preferably, the polypeptide comprises the amino acid sequences of (i) both SEQ ID NOs: 15 and 16, (ii) both SEQ ID NOs: 23 and 24, (iii) both SEQ ID NOs: 31 and 32, or (iv) both SEQ ID NOs: 39 and 40.

In an embodiment of the invention, the inventive polypeptide can further comprise the constant region of the inventive TCR set forth above. In this regard, the polypeptide can further comprise the amino acid sequence of SEQ ID NO: 41 (human constant region of α chain), SEQ ID NO: 42 (human constant region of β chain), SEQ ID NO: 43 (human constant region of β chain), SEQ ID NO: 44 (WT murine constant region of α chain), SEQ ID NO: 45 (WT murine constant region of β chain), SEQ ID NO: 46 (substituted murine constant region of α chain), SEQ ID NO: 47 (substituted murine constant region of β chain), SEQ ID NO: 48 (cysteine-substituted, hydrophobic amino acid-substituted murine constant region of α chain), SEQ ID NO: 49 (cysteine-substituted, hydrophobic amino acid-substituted murine constant region of α chain), both SEQ ID NOs: 44 and 45, both SEQ ID NOs: 46 and 47, or both SEQ ID NOs: 48 and 49, both SEQ ID NOs: 41 and 42, or both SEQ ID NOs: 41 and 43. Preferably, the polypeptide further comprises the amino acid sequences of (i) both SEQ ID NOs: 44 and 45, (ii) both SEQ ID NOs: 46 and 47, (iii) both SEQ ID NOs: 48 and 49, (iv) both SEQ ID NOs: 41 and 42, or (v) both SEQ ID NOs: 41 and 43 in combination with any of the CDR regions or variable regions described herein with respect to other aspects of the invention.

In an embodiment of the invention, the inventive polypeptide can comprise the entire length of an α or β chain of the TCR described herein. In this regard, the inventive polypeptide can comprise the amino acid sequence of SEQ ID NO: 50, SEQ ID NO: 51, SEQ ID NO: 52, SEQ ID NO: 53, SEQ ID NO: 54, SEQ ID NO: 55, SEQ ID NO: 56, or SEQ ID NO: 57. Alternatively, the polypeptide of the invention can comprise both chains of the TCRs described herein. For example, the polypeptide of the invention can comprise both amino acid sequences of SEQ ID NOs: 50 and 51, both SEQ ID NOs: 52 and 53, both SEQ ID NOs: 54 and 55, or both SEQ ID NOs: 56 and 57. Preferably, the polypeptide comprises the amino acid sequences of (1) both SEQ ID NOs: 50-51; (2) both SEQ ID NOs: 52-53; (3) both SEQ ID NOs: 54-55; or (4) both SEQ ID NOs: 56-57.

The invention further provides a protein comprising at least one of the polypeptides described herein. By "protein" is meant a molecule comprising one or more polypeptide chains.

In an embodiment, the protein of the invention can comprise (a) a first polypeptide chain comprising the amino acid sequences of SEQ ID NOs: 9-11 and a second polypeptide chain comprising the amino acid sequence of SEQ ID NOs: 12-14; (b) a first polypeptide chain comprising the amino acid sequences of SEQ ID NOs: 17-19 and a second polypeptide chain comprising the amino acid sequences of SEQ ID NOs: 20-22; (c) a first polypeptide chain comprising the amino acid sequences of SEQ ID NOs: 25-27 and a second polypeptide chain comprising the amino acid sequences of SEQ ID NOs: 28-30; or (d) a first polypeptide chain comprising the amino acid sequences of SEQ ID NOs: 33-35 and a second polypeptide chain comprising the amino acid sequences of SEQ ID NOs: 36-38.

In another embodiment of the invention, the protein may comprise (i) a first polypeptide chain comprising the amino acid sequences of SEQ ID NO: 15 and a second polypeptide chain comprising the amino acid sequences of SEQ ID NO: 16; (ii) a first polypeptide chain comprising the amino acid sequences of SEQ ID NO: 23 and a second polypeptide chain comprising the amino acid sequences of SEQ ID NO: 24; (iii) a first polypeptide chain comprising the amino acid sequences of SEQ ID NO: 31 and a second polypeptide chain comprising the amino acid sequences of SEQ ID NO: 32; or (iv) a first polypeptide chain comprising the amino acid sequences of SEQ ID NO: 39 and a second polypeptide chain comprising the amino acid sequences of SEQ ID NO: 40.

The inventive protein may further comprise any of the constant regions described herein with respect to other aspects of the invention. In this regard, in an embodiment of the invention, the first polypeptide chain may further comprise the amino acid sequence of SEQ ID NO: 46, wherein: (i) X at position 48 of SEQ ID NO: 46 is Thr or Cys; (ii) X at position 112 of SEQ ID NO: 46 is Ser, Ala, Val, Leu, Ile, Pro, Phe, Met, or Trp; (iii) X at position 114 of SEQ ID NO: 46 is Met, Ala, Val, Leu, Ile, Pro, Phe, or Trp; and (iv) X at position 115 of SEQ ID NO: 46 is Gly, Ala, Val, Leu, Ile, Pro, Phe, Met, or Trp; and (B) the second polypeptide chain may further comprise the amino acid sequence of SEQ ID NO: 47, wherein X at position 57 of SEQ ID NO: 47 is Ser or Cys. In another embodiment of the invention, the first polypeptide chain may further comprise the amino acid sequence of SEQ ID NO: 41 (constant region of human α chain), SEQ ID NO: 44 (WT constant region of murine α chain), or SEQ ID NO: 48 (cysteine-substituted, hydrophobic amino acid-substituted murine constant region of α chain), and the second polypeptide chain may further comprise the amino acid sequence of SEQ ID NO: 42 (constant region of human β chain), SEQ ID NO: 43 (constant region of human β chain), SEQ ID NO: 45 (WT constant region of murine β chain), or SEQ ID NO: 49 (cysteine-substituted, hydrophobic amino acid-substituted murine constant region of β chain).

Alternatively or additionally, the protein of the invention can comprise (1) a first polypeptide chain comprising the amino acid sequence of SEQ ID NO: 50 and a second polypeptide chain comprising the amino acid sequence of SEQ ID NO: 51; (2) a first polypeptide chain comprising the amino acid sequence of SEQ ID NO: 52 and a second polypeptide chain comprising the amino acid sequence of SEQ ID NO: 53; (3) a first polypeptide chain comprising the amino acid sequence of SEQ ID NOs: 54 and a second polypeptide chain comprising the amino acid sequence of SEQ ID NO: 55; or (4) a first polypeptide chain comprising the amino acid sequence of SEQ ID NOs: 56 and a second polypeptide chain comprising the amino acid sequence of SEQ ID NO: 57. In this instance, the protein of the invention can be a TCR. Alternatively, if, for example, the protein comprises a single polypeptide chain comprising the amino acid sequences of both SEQ ID NOs: 50 and 51, both SEQ ID NOs: 52 and 53, both SEQ ID NOs: 54 and 55, or both SEQ ID NOs: 55 and 56, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods.

In some embodiments of the invention, the TCRs, polypeptides, and proteins of the invention may be expressed as a single protein comprising a linker peptide linking the α chain and the β chain. In this regard, the TCRs, polypeptides, and proteins of the invention may further comprise a linker peptide. The linker peptide may advantageously facilitate the expression of a recombinant TCR, polypeptide, and/or protein in a host cell. The linker peptide may comprise any suitable amino acid sequence. For example, the linker peptide may comprise SEQ ID NO: 58. Upon expression of the construct including the linker peptide by a host cell, the linker peptide may be cleaved, resulting in separated α and β chains. In an embodiment of the invention, the TCR, polypeptide, or protein may comprise an amino acid sequence comprising a full-length α chain, a full-length β chain, and a linker peptide positioned between the α and β chains.

The protein of the invention can be a recombinant antibody, or an antigen binding portion thereof, comprising at least one of the inventive polypeptides described herein. As used herein, "recombinant antibody" refers to a recombinant (e.g., genetically engineered) protein comprising at least one of the polypeptides of the invention and a polypeptide chain of an antibody, or an antigen binding portion thereof. The polypeptide of an antibody, or antigen binding portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or an antigen binding portion thereof, can exist as a separate polypeptide of the recombinant antibody. Alternatively, the polypeptide chain of an antibody, or an antigen binding portion thereof, can exist as a polypeptide, which is expressed in frame (in tandem) with the polypeptide of the invention. The polypeptide of an antibody, or an antigen binding portion thereof, can be a polypeptide of any antibody or any antibody fragment, including any of the antibodies and antibody fragments described herein.

Included in the scope of the invention are functional variants of the inventive TCRs, polypeptides, or proteins described herein. The term "functional variant," as used herein, refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to mutated KRAS for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 95%, 96%, 97%, 98%, 99% or more identical in amino acid sequence to the parent TCR, polypeptide, or protein, respectively.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR, polypeptide, or protein can consist essentially of the specified amino acid sequence or sequences described herein, such that other components of the TCR, polypeptide, or protein, e.g., other amino acids, do not materially change the biological activity of the TCR, polypeptide, or protein. In this regard, the inventive TCR, polypeptide, or protein can, for example, consist essentially of the amino acid sequence of SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, (1) both of SEQ ID NOs: 50-51; (2) both of SEQ ID NOs: 52-53; (3) both of SEQ ID NOs: 54-55; or (4) both of SEQ ID NOs: 56-57. Also, for instance, the inventive TCRs, polypeptides, or proteins can consist essentially of the amino acid sequence(s) of SEQ ID NO: 15, SEQ ID NO: 16, SEQ ID NO: 23, SEQ ID NO: 24, SEQ ID NO: 31, SEQ ID NO: 32, SEQ ID NO: 39, SEQ ID NO: 40, (i) both of SEQ ID NOs: 15-16; (ii) both of SEQ ID NOs: 23-24; (iii) both of SEQ ID NOs: 31-32; or (iv) both of SEQ ID NOs: 39-40. Furthermore, the inventive TCRs, polypeptides, or proteins can consist essentially of the amino acid sequences of (a) all of SEQ ID NOs: 9-14; (b) all of SEQ ID NOs: 17-22; (c) all of SEQ ID NOs: 25-30; or (d) all of SEQ ID NOs: 33-38.

The TCRs, polypeptides, and proteins of the invention can be of any length, i.e., can comprise any number of amino acids, provided that the TCRs, polypeptides, or proteins retain their biological activity, e.g., the ability to specifically bind to mutated KRAS; detect cancer in a mammal; or treat or prevent cancer in a mammal, etc. For example, the polypeptide can be in the range of from about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention can be glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention can be obtained by methods known in the art such as, for example, de novo synthesis. Also, polypeptides and proteins can be recombinantly produced using the nucleic acids described herein using standard recombinant methods. See, for instance, Green and Sambrook, *Molecular Cloning: A*

Laboratory Manual, 4th ed., Cold Spring Harbor Press, Cold Spring Harbor, N.Y. (2012). Alternatively, the TCRs, polypeptides, and/or proteins described herein can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs, polypeptides, and proteins can be synthetic, recombinant, isolated, and/or purified.

Included in the scope of the invention are conjugates, e.g., bioconjugates, comprising any of the inventive TCRs, polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art.

An embodiment of the invention provides a nucleic acid comprising a nucleotide sequence encoding any of the TCRs, polypeptides, or proteins described herein. "Nucleic acid," as used herein, includes "polynucleotide," "oligonucleotide," and "nucleic acid molecule," and generally means a polymer of DNA or RNA, which can be single-stranded or double-stranded, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green and Sambrook et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the TCRs, polypeptides, or proteins described herein. In an embodiment of the invention, the nucleic acid may comprise the nucleotide sequences of any one of SEQ ID NOs: 63-70 (Table 1). In an embodiment of the invention, the nucleic acid comprises the nucleotide sequences of both of SEQ ID NOs: 63-64, both of SEQ ID NOs: 65-66, both of SEQ ID NOs: 67-68, or both of SEQ ID NOs: 69-70.

TABLE 1

| TCR ID | TCR chain | Nucleotide sequence of the indicated TCR chain variable region |
|---|---|---|
| 1 | Alpha (TRAV4*01) | SEQ ID NO: 63 (wild-type) |
|   | Beta (TRBV5-6*01) (A) | SEQ ID NO: 64 (wild-type) |
| 2 | Alpha (TRAV4*01) | SEQ ID NO: 65 (codon-optimized) |
|   | Beta (TRBV5-6*01) (C) | SEQ ID NO: 66 (codon-optimized) |
| 3 | Alpha (TRAV4*01) | SEQ ID NO: 67 (wild-type) |
|   | Beta (TRBV5-6*01) (B) | SEQ ID NO: 68 (wild-type) |
| 4 | Alpha (TRAV12-2*01) | SEQ ID NO: 69 (wild-type) |
|   | Beta (TRBV10-2*01) | SEQ ID NO: 70 (wild-type) |

In an embodiment of the invention, the nucleic acid comprises a codon-optimized nucleotide sequence encoding any of the TCRs, polypeptides, or proteins described herein. Without being bound to any particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein. In this regard, the nucleic acid may consist essentially of any of the nucleotide sequences described herein.

The nucleic acids of the invention can be incorporated into a recombinant expression vector. In this regard, the invention provides a recombinant expression vector comprising any of the nucleic acids of the invention. In an embodiment of the invention, the recombinant expression vector comprises a nucleotide sequence encoding the α chain, the β chain, and linker peptide.

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotide, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector. In an especially preferred embodiment, the recombinant expression vector is an MSGV1 vector.

The recombinant expression vectors of the invention can be prepared using standard recombinant DNA techniques described in, for example, Green and Sambrook et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein, or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, nitroreductase, and the inducible caspase 9 gene system.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD4^+$ T cells, $CD8^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods*, 128:189-201 (1990). In an embodiment, expansion of the numbers of T cells is carried out by culturing the T cells with OKT3 antibody, IL-2, and feeder PBMC (e.g., irradiated allogeneic PBMC).

The inventive TCRs, polypeptides, proteins, nucleic acids, recombinant expression vectors, and host cells (including populations thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70%, 80%, 90%, 95%, or can be 100%.

The inventive TCRs, polypeptides, proteins, nucleic acids, recombinant expression vectors, and host cells (including populations thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, nucleic acids, expression vectors, and host cells (including populations thereof), described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Methods for preparing administrable compositions are known or apparent to those skilled in the art and are described in more detail in, for example, *Remington: The Science and Practice of Pharmacy*, $22^{nd}$ Ed., Pharmaceutical Press (2012). It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell expressing the inventive TCR, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen (e.g., mutated KRAS), or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, polypeptide, or protein upon administration of a given dose of such T cells to a mammal among a set of mammals of which each is given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the cancer being treated. In an embodiment in which the inventive TCR material is a population of cells, the number of cells administered per infusion may vary, e.g., from about $1 \times 10^6$ to about $1 \times 10^{12}$ cells or more. In certain embodiments, fewer than $1 \times 10^6$ cells may be administered.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a chemotherapeutic agent. The practice of conjugating compounds to a chemotherapeutic agent is known in the art. One of ordinary skill in the art recognizes that sites on the inventive TCR materials, which are not necessary for the function of the inventive TCR materials, are ideal sites for attaching a bridge and/or a chemotherapeutic agent, provided that the bridge and/or chemotherapeutic agent, once attached to the inventive TCR materials, do(es) not interfere with the function of the inventive TCR materials, i.e., the ability to bind to mutated KRAS or to detect, treat, or prevent cancer.

It is contemplated that the inventive pharmaceutical compositions, TCRs, polypeptides, proteins, nucleic acids, recombinant expression vectors, host cells, and populations of cells can be used in methods of treating or preventing cancer. Without being bound to a particular theory, the inventive TCRs are believed to bind specifically to mutated KRAS, such that the TCR (or related inventive polypeptide or protein), when expressed by a cell, is able to mediate an immune response against a target cell expressing mutated KRAS. In this regard, the invention provides a method of treating or preventing cancer in a mammal, comprising administering to the mammal any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to treat or prevent cancer in the mammal.

An embodiment of the invention provides any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, for use in the treatment or prevention of cancer in a mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the cancer, or a symptom or condition thereof. Alternatively or additionally, "prevention" may encompass preventing or delaying the recurrence of cancer, or a symptom or condition thereof.

Also provided is a method of detecting the presence of cancer in a mammal. The method comprises (i) contacting a sample comprising one or more cells from the mammal with any of the inventive TCRs, polypeptides, proteins, nucleic acids, recombinant expression vectors, host cells, populations of cells, or pharmaceutical compositions described herein, thereby forming a complex, and detecting the complex, wherein detection of the complex is indicative of the presence of cancer in the mammal.

With respect to the inventive method of detecting cancer in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive TCRs, polypeptides, proteins, nucleic acids, recombinant expression vectors, host cells, or populations of cells, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, colorectal cancer, endometrial cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer is pancreatic, colorectal, lung, endometrial, ovarian, or prostate cancer. Preferably, the lung cancer is lung adenocarcinoma, the ovarian cancer is epithelial ovarian cancer, and the pancreatic cancer is pancreatic adenocarcinoma. In another preferred embodiment, the cancer is a cancer that expresses the mutated KRAS amino acid sequence with the G12D mutation.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

EXAMPLES

Next-Generation Sequencing

Genomic DNA (gDNA) and total RNA was purified from various tumors and matched normal apheresis samples using the QIAGEN ALLPREP DNA/RNA kit (Qiagen, Venlo, Netherlands) following the manufacturer's suggestions. One sample (Tu-Pri) was formalin-fixed, paraffin-embedded (FFPE) and gDNA was extracted using the Covaris TRUX-TRAC™ FFPE DNA kit, as directed by the manufacturer (Covaris, Woburn, Mass.). Whole-exome library construction and exon capture of approximately 20,000 coding genes was prepared using Agilent Technologies SURESELECTXT target enrichment system for paired-end libraries coupled with Human ALL EXON V6 RNA bait (Agilent Technologies, Santa Clara, Calif., USA). Whole-exome sequencing (WES) libraries were subsequently sequenced on a NEXTSEQ 500 desktop sequencer (Illumina, San Diego, Calif., USA). The library was prepped using 3 µg gDNA from fresh tumor tissue samples and 200 ng gDNA from the FFPE tumor sample following manufacturer's protocol. Paired-end sequencing was done with an ILLUMINA high-output flow cell kit (300 cycles) using initially v1 of the reagent/flow cell kit followed by a subsequent run of the same library prep on v2 of reagent/flow cell kit. RNA-seq libraries were prepared using 2 µg of total RNA with the ILLUMINA TRUSEQ RNA stranded library prep kit following the manufacturer's protocol. RNA-seq libraries were paired-end sequenced on a NEXTSEQ 500 desktop sequencer (Illumina, San Diego, Calif., USA).

Alignment, Processing and Variant Calling

For WES, alignments were performed using NOVOALIGN MPI program from Novocraft (Selangor, Malaysia) (novocraft.com/) to human genome build hg19. Duplicates were marked using Picard's MARKDUPLICATES tool. In/del realignment and base recalibration was carried out according to the GATK best practices workflow (broadinstitute.org/gatk/). Post cleanup of data, SAMTOOLS utility (samtools.sourceforge.net) was used to create pileup files and VARSCAN2 platform-independent mutation caller (varscan.sourceforge.net) was used to call somatic variants using the following criteria: tumor and normal read counts of 10 or greater, variant allele frequency of 10% or greater and tumor variant reads of 4 or more. These variants were then annotated using ANNOVAR software tool (annovar.openbioinformatics.org).

For RNA-seq, alignments were performed using the STAR (github.com/alexdobin/STAR) two pass method to human genome build hg19. Duplicates were marked using Picard's MARKDUPLICATES tool. Reads were split and trimmed using GATK SPLITNTRIM tool. After which In/del realignment and base recalibration were performed using GATK toolbox. A pileup file was created using the final recalibrated bam file and SAMTOOLS MPILEUP tool. Finally, variants were called using VARSCAN2 platform-independent mutation caller.

WES and RNA-seq was carried out on three metastatic fresh tumor samples (Tu-1, Tu-2A, and Tu-2B). Variants with a minimum exome frequency of 7% and a minimum of three alternate reads were then manually curated using the Integrated Genomics Viewer (IGV) tool (Broad Institute, Cambridge, Mass.) in order to remove false positive calls that appeared to result from sequencing or mapping errors. In an attempt to focus on mutations that were likely to be clonal or represented in dominant clonal populations, 61 mutations were chosen for further analysis based upon their detection in more two or more tumor samples. One of these 61 mutations was KRAS (Table 2). These included 29 that were identified in a minimum of one WES and one RNA-seq library, and 32 that were identified in WES libraries from two or more of the metastatic lesions.

TABLE 2

| Gene Symbol | KRAS |
| --- | --- |
| Transcript ID | NM_004985 |
| Mutation Position | chr12: 25398284 |
| Mutation Type* | NS SNV |
| cDNA Change | c.G35A |
| Amino Acid Change | p.G12D |
| % Mutant Reads† (Exome) | 27 |
| % Mutant Reads† (RNA) | 38 |
| FPKM‡ | 7.94 |

Generation of Tumor Infiltrating Lymphocytes (TILs), Infusion TILs, and Antigen Presenting Dendritic Cells (DCs)

TILs, infusion TILs, and dendritic cells were generated as described in Tran et al., *Science*, 350: 1387-90 (2015). Briefly, to generate TILs, surgically resected tumors were cut into twenty-four fragments approximately 1-2 mm in size and each fragment was placed into a separate well of a 24-well plate containing 2 ml of complete media (CM) containing high dose IL-2 (6000 IU/ml, Chiron, Emeryville, Calif.). CM contained RPMI media supplemented with 10% in-house human serum, 2 mM L-glutamine, 25 mM HEPES and 10 μg/ml gentamicin. TIL fragment culture #6 was selected for treatment and thus underwent a rapid expansion procedure in gas-permeable G-REX100 flasks using irradiated PBMC at a ratio of 1 to 100 in 400 ml of 50/50 medium, supplemented with 5% human AB serum, 3000 IU/ml of IL-2, and 30 ng/ml of OKT3 antibody (Miltenyi Biotec, Bergisch Gladbach, Germany). 50/50 media contained a 1 to 1 mixture of CM with AIM-V media. All cells were cultured at 37° C. with 5% $CO_2$.

Immature DCs were generated from peripheral blood monocytes using the plastic adherence method. Briefly, patient apheresis was thawed, washed, set to 7.5-10e6 cells/ml with AIM-V media (Life Technologies, Carlsbad, Calif.) and then incubated at approximately 1e6 cells/$cm^2$ in tissue culture flasks (162 $cm^2$ surface area) and incubated at 37° C., 5% $CO_2$. After 90 minutes (min), the non-adherent cells were collected and the adherent cells in the flasks were vigorously washed with AIM-V media, and then further incubated with AIM-V media for 60 min. The media and non-adherent cells were removed and the adherent cells in the flasks were then vigorously washed again with AIM-V media and then incubated with DC media. DC media contained RPMI containing 5% human serum, 100 U/ml penicillin and 100 μg/ml streptomycin, 2 mM L-glutamine, 800 IU/ml GM-CSF (LEUKINE (sargramostim)) and 200 U/ml IL-4 (Peprotech, Rocky Hill, N.J.). On day 2-3, fresh DC media was added to the cultures. DCs were cryopreserved on day 4 or 5 after initiation of the culture. DCs were used in experiments between day 4 and day 6 post initiation of the cultures.

Identification of Mutation-Reactive T Cells and Co-Culture Experiments

The detailed methods are described in Tran et al., Science, 350: 1387-90 (2015). Briefly, sixty-one mutations were identified by whole-exome and transcriptome sequencing. One of these 61 mutations was KRAS (Table 2). For each mutation, a minigene encoding the mutation flanked by 12 amino acids on either side with the parent protein was generated and synthesized in tandem to create tandem minigene (TMG) constructs. Five TMGs (TMGs 1-5) encoding the 61 mutations were made, in vitro transcribed into RNA, and then electroporated into autologous antigen presenting DCs allowing for the processing and presentation of all mutations in the context of the patient's own HLA-I and HLA-II molecules (Table 4). The TMGs for wild-type and mutated KRAS are shown in Table 3. The HLA data shown in Table 4 was determined from next generation sequencing data using the algorithm PHLAT as described in Bai et al., BMC Genomics, 15: 325 (2014). Twenty-four individual TIL cultures from the patient were then cocultured with these TMG-expressing DCs, and T-cell reactivity was determined by IFN-γ enzyme-linked immunospot (ELISPOT) assay (FIG. 1A) and flow cytometric analysis of the T-cell activation markers 4-1BB and OX40. Multiple TIL cultures that were reactive against TMG-1 were identified. To identify which mutated antigen in TMG-1 was being recognized by TIL culture #6, the peptides that were encoded in TMG-1 were synthesized (ThermoFisher Scientific (Waltham, Mass.) and GenScript Inc. (Piscataway Township, N.J.)) and then individually pulsed onto DCs overnight followed by co-culture with TIL culture #6 (FIG. 1B).

TABLE 3

| Gene Symbol | KRAS |
|---|---|
| Amino Acid Change | p.G12D |
| Wild-Type Minigene (Amino Acid) | MTEYKLVVVGAGGVGKSALTIQLI (SEQ ID NO: 61) |
| Mutated Minigene (Amino Acid) | MTEYKLVVVGADGVGKSALTIQLI (SEQ ID NO: 62) |
| TMG Construct | 1 |

TABLE 4

| HLA-I | | | | | | HLA-II | | | | | |
|---|---|---|---|---|---|---|---|---|---|---|---|
| A | A | B | B | C | C | DRB1 | DRB1 | DQA1 | DQA1 | DQB1 | DQB1 |
| 02:01 | 03:01 | 14:01 | 44:03 | 08:02 | 16:01 | 07:01 | | 02:01 | | 02:02 | |

The following HPLC purified peptides (GenScript Inc.) were used in peptide titration experiments: wild-type (WT)-9mer: GAGGVGKSA (SEQ ID NO: 7); mutated (G12D)-9mer: GADGVGKSA (SEQ ID NO: 8); WT-10mer: GAGGVGKSAL (SEQ ID NO: 5); G12D-10mer: GADGVGKSAL (SEQ ID NO: 6).

Intracellular cytokine staining (ICS) and flow cytometry was used to determine the expression of the cytokines IFN-γ, TNF, and IL-2, and the degranulation marker CD107a as described in Tran et al., Science, 344: 641-5 (2014). Briefly, target and effector cells were combined in the wells of a 96-well plate and both GOLGISTOP and GOLGIPLUG protein transport inhibitors (both at ½ the recommended concentrations) were added to the culture (BD Biosciences, Franklin Lakes, N.J.). At t=6 h post stimulation, cells were processed using the CYTOFIX/CYTOPERM kit (BD Biosciences) according to the manufacturer's instructions. Cells were acquired on a FACSCANTOII flow cytometer and data were analyzed using FLOWJO software (TreeStar Inc., Ashland, Oreg.). Boolean gate analysis was used to determine the percentage of cells expressing the indicated number of effector functions (cytokines and degranulation marker).

Identification of $KRAS^{G12D}$-Reactive T-Cell Clones

Four $KRAS^{G12D}$-reactive TCRs were identified using various methods. The dominant TRBV5-6 (Vβ5.2) clone in the infusion bag was isolated from TIL fragment culture #6 prior to rapid expansion. Briefly, TIL culture #6 was stained with the anti-Vβ5.2-PE (phycoerythrin) antibody (Beckman Coulter, Schaumburg, Ill.) and the Vβ5.2+ cells were enriched using anti-PE specific antibodies conjugated to magnetic microbeads as directed by the manufacturer (Miltenyi Biotec). Total RNA was isolated from the Vβ5.2+ T cells (RNEASY MINI kit, Qiagen) and then underwent 5'RACE as directed by manufacturer (SMARTER RACE cDNA amplification kit, Clontech) using TCR-alpha and beta chain constant primers. The sequences of the alpha and beta chain constant primers were: TCR-alpha, 5'—GCC ACA GCA CTG TTG CTC TTG AAG TCC—3' (SEQ ID NO: 59); TCR-beta, 5'—CAG GCA GTA TCT GGA GTC ATT GAG—3 (SEQ ID NO: 60). Program 1 of the kit was used for the PCR, with a modification to the extension time (2 min instead of 3 min). TCR PCR products were then isolated by standard agarose gel electrophoresis and gel extraction (zymogen) and products were then sequenced (Macrogen, Seoul, Korea).

The second and third ranked TCRs in the infusion bag were also $KRAS^{G12D}$-reactive and were isolated by first stimulating the day 40 post-cell transfer apheresis sample with DCs pulsed overnight with $KRAS^{G12D}$ long peptides. Vβ5.2-positive and negative CD8+ T cells that upregulated the T-cell activation marker 4-1BB after overnight stimulation were then sorted separately by FACS. The Vβ5.2+ cells were further expanded prior to undergoing 5'RACE as described above, followed by TOPO-TA cloning of the TCR PCR products and sequencing of individual colonies to identify the TCR-alpha and beta chains. The Vβ5.2-negative cells underwent single-cell, multiplex TCR PCR to identify the TCR-alpha and beta chains as described in Pasetto et al., *Cancer Immunol. Res.*, (2016).

The fourth $KRAS^{G12D}$-reactive TCR (ranked 45$^{th}$ in the infusion bag) was identified from a different TIL fragment (TIL fragment #5) using another single-cell technology approach. Briefly, TIL culture #5 was co-cultured with DCs transfected with TMG-1 (which encodes for $KRAS^{G12D}$) and after 4 hours (h), the TILs were harvested and subjected to the FLUIDIGM C1 system (Fluidigm, San Francisco, Calif.) to prepare single-cell RNA-seq samples according to the manufacturer's protocol. Single-cell RNA-seq samples were then sequenced by the ILLUMINA MISEQ system and the data were analyzed by an in-house bioinformatics program. TCR-alpha and beta sequences were extracted from samples that demonstrated an upregulation of IFN-γ transcripts upon stimulation.

In Vivo Tracking of $KRAS^{G12D}$-Reactive T Cells

To determine the frequencies of the $KRAS^{G12D}$-reactive T cells in the samples, the TCR sequences of the $KRAS^{G12D}$-reactive T-cell clones were first identified, and these sequences were interrogated against the TCR-Vβ deep sequencing data from the indicated samples. The number of in-frame productive TCR reads in the samples ranged between 522,499 to 1,990,345.

Flow Cytometry Antibodies

The following anti-human flow cytometry antibodies were used in this report: CD3-AF700 (clone: UCHT1, BioLegend), CD8-PE-Cy7 (clone: SK1, BD Biosciences), CD4-APC-Cy7 (clone: SK3, BioLegend), OX40-FITC (clone: Ber-ACT35, BD Biosciences), 4-1BB-APC (clone: 4B4-1, BioLegend), and Vβ5.2-PE (Beckman Coulter). Fluorochrome conjugated anti-mouse TCR-beta constant region antibody (H57-597, eBioscience) was used to evaluate transduction efficiency of the TCRs. The IO TEST Beta Mark TCR V kit was used to assess the TCR-Vβ repertoire (Beckman Coulter).

Identification of Mutation-Reactive T Cells and Generation of Infusion Product

A previously described method (Lu et al., *Clin. Cancer Res.,* 20: 3401-10 (2014); Tran et al., *Science,* 344: 641-5 (2014); Tran et al., *Science,* 350: 1387-90 (2015)) was used to test whether TILs from patient 4095 recognized somatic mutations expressed by her metastatic lung tumors. TIL culture #6 contained the highest frequency of $KRAS^{G12D}$-reactive CD8+ T cells and thus underwent a two-week rapid expansion procedure prior to cell infusion as described in Tran et al., *Science,* 344: 641-5 (2014).

In Vivo Tracking of $KRAS^{G12D}$-Specific T-Cell Clones

T-cell receptor (TCR)-Vβ deep sequencing was performed on gDNA isolated from the patient's infusion product, 3 separate lung nodules prior to treatment, the progressing lesion (Lesion 3), and on peripheral blood prior to and at various times after cell infusion (Adaptive Biotechnologies, Seattle Wash.) to interrogate the frequency of $KRAS^{G12D}$-reactive TCR sequences.

Assessing Reactivity of $KRAS^{G12D}$-Specific TCRs

Four $KRAS^{G12D}$-reactive TCRs were identified, and the TCR-alpha and beta chain sequences were synthesized and then cloned into the MSGV1 retroviral vector (GenScript Inc.). Retroviral supernatants encoding the TCRs were generated and used to transduce autologous peripheral blood T cells as described in Tran et al., *Science,* 344: 641-5 (2014). TCR-transduced T cells were then co-cultured with autologous peripheral blood mononuclear cells (PBMCs) loaded with titrating doses of various KRAS peptides, or $KRAS^{G12D}$-positive pancreatic cancer cell lines stably expressing or not expressing the restricting HLA-C*08:02 allele (Tran et al., *Science,* 350: 1387-90 (2015)). T-cell reactivity was determined the next day by IFN-γ ELISPOT assay and flow cytometric analysis of the T-cell activation markers 4-1BB and OX40 (Tran et al., *Science,* 350: 1387-90 (2015)).

Example 1

This example demonstrates the in vivo frequency of $KRAS^{G12D}$ mutation-reactive CD8+ T cells.

The patient was a 49-year old female with colorectal adenocarcinoma and multiple bilateral pulmonary metastases. She previously received 12 cycles of FOLFOX chemotherapy after a sigmoid colectomy and partial cystectomy, followed by 4182 cGy radiation to the bladder suture line. Shortly after this, she experienced an increase in the number and size of FDG avid bilateral pulmonary nodules. Biopsy of a right lower lobe nodule was consistent with metastatic colorectal adenocarcinoma.

The patient was enrolled on the institutional review board-approved phase II clinical trial (ClinicalTrials.gov number, NCT01174121) designed to test whether the adoptive transfer of ex vivo expanded tumor-infiltrating lymphocytes (TILs) containing T cells targeting cancer mutations can mediate regression of metastatic solid cancers. Baseline CT scans revealed lung disease as the sole source of cancer progression. Three lung lesions were resected using video-assisted thoracoscopic surgery (VATS) and 24 individual TIL cultures were generated from multiple tumor fragments. The 3 lesions also underwent whole-exomic and transcriptome sequencing to identify mutations expressed by the tumors (Table 2). Each TIL culture was evaluated for reactivity against these mutations. It was found that the patient's TILs contained CD8+ T cells that specifically recognized the $KRAS^{G12D}$ mutation (FIGS. 1A and B). The TIL culture that displayed the highest frequency of $KRAS^{G12D}$-reactive CD8+ T cells was selected. The numbers of selected cells were expanded for treatment (FIGS. 1B and C). Prior to cell infusion, the patient underwent a non-myeloablative, lymphodepleting chemotherapy regimen including 60 mg/kg cyclophosphamide for 2 days, followed by 25 mg/m$^2$ fludarabine for 5 days (Dudley et al., *J. Clin. Oncol.,* 23: 2346-57 (2005)). The patient received a single infusion of $1.48 \times 10^{11}$ TILs, followed by 5 doses of interleukin-2 (IL-2) at 720,000 IU/kg, stopping for fatigue.

The therapy was well tolerated and the patient was sent home two weeks after cell infusion. Approximately 75% of the infusion product contained CD8+ T cells that specifically recognized the KRAS$^{G12D}$ mutation, and the majority of these T cells produced multiple effector cytokines (IFN-γ, TNF, and IL-2) and displayed cytolytic potential. All 7 metastatic lung lesions regressed at the first follow up 40 days-post cell transfer, and 6/7 lesions continued to regress or completely respond until one lesion (Lesion 3) progressed at approximately 9 months-post therapy. A VATS resection of the left lower lung was performed at approximately 9 months-post cell transfer to remove the sole progressing lesion (Lesion 3) as well as a responding lesion (Lesion 2) that was PET negative and completely necrotic with no live tumor cells on pathological analysis. The patient remains clinically disease free 3 months after the lung resection.

The infusion TIL product contained at least four KRAS$^{G12D}$-reactive T-cell clonotypes of varying frequencies. The three highest frequency TCRs in the infusion product were reactive against KRAS$^{G12D}$, comprising of 49.5%, 19.1%, and 6.9% of the infusion bag, while a fourth KRAS$^{G12D}$-reactive TCR was the 45$^{th}$ most frequent and was present at only 0.04% of the infusion bag (FIGS. 2A-2D and Table 5). None of these KRAS$^{G12D}$-reactive TCRs were detected (frequency<0.0002%) in the peripheral blood of the patient one week prior to infusion (FIGS. 2A-2D). After cell transfer, dramatic differences in the engraftment of the KRAS$^{G12D}$-reactive TCRs were observed. The most dominant infused T-cell clonotype (~7.3×10$^{10}$ cells) was not detected in the blood 40 days-post cell transfer, while the remaining KRAS$^{G12D}$-reactive T-cell clones were detected at this time point (FIGS. 2A-2D). The KRAS$^{G12D}$-reactive T-cell clones persisting in the peripheral blood represented 10.4%, 4.5%, and 0.005% of all peripheral blood T cells at approximately 9 months-post cell transfer, and the most dominant T-cell clone in the peripheral blood at that time was the TRBV10-02 mutant KRAS$^{G12D}$-reactive TCR (FIGS. 2A-2D and Table 5). There did not appear to be an enrichment of the KRAS$^{G12D}$-reactive T-cell clones in the progressing tumor relative to the peripheral blood (FIGS. 2A-2D).

Example 2

This example demonstrates the specificity and sensitivity of the KRAS$^{G12D}$-reactive TCRs.

The nucleotide sequence encoding the TCR was cloned from each of the four KRAS$^{G12D}$-reactive T-cell clonotypes of Example 1. Each TCR was cloned into an MSGV1-retroviral vector. The amino acid sequences of the alpha and beta chains of each of the four TCRs is shown in Table 6.

TABLE 6

| TCR-α/TCR-β Gene Name | Variable Region Alpha Chain Amino Acid Sequence | Variable Region Beta Chain Amino Acid Sequence |
|---|---|---|
| TRAV4/TRBV5-6 (A) | SEQ ID NO: 15 | SEQ ID NO: 16 |
| TRAV12-2/TRBV10-2 | SEQ ID NO: 39 | SEQ ID NO: 40 |
| TRAV4/TRBV5-6 (B) | SEQ ID NO: 31 | SEQ ID NO: 32 |
| TRAV4/TRBV5-6 (C) | SEQ ID NO: 23 | SEQ ID NO: 24 |

The nucleotide sequence cloned into the MSGV1-retroviral vector encoded the variable region of the TCR alpha chain (shown in Table 6) and the murine TCR alpha chain constant region, followed by a P2A linker sequence (SEQ ID NO: 58) and a nucleotide sequence encoding the variable region of the TCR beta chain (shown in Table 6) and the murine TCR beta chain constant region. The TCR was further modified to include cysteine substitutions in the murine constant region of both of the α and β chains in combination with a substitution(s) of three amino acids in the TM domain of the murine constant region of the alpha chain with a hydrophobic amino acid. The full-length amino acid sequence of each of the four TCRs is shown in Table 7. Without being bound to a particular theory or mechanism, it is believed that the murine TCR alpha and beta constant chains may diminish mispairing with endogenous TCRs and may promote the expression of the introduced TCRs by the host cells. It is also believed that enhanced expression and pairing of the introduced TCR alpha and beta chains may be achieved by incorporating hydrophobic amino acids in the

TABLE 5

| Patient ID | TCR-α/ TCR-β Gene Name | TCR-α/TCR-β CDR3 Amino Acid Sequence | Frequency in Tumor Samples† | Rank in Tumor Samples† | Frequency in Infusion Product | Rank in Infusion Product | Frequency in Blood on d + 266 | Rank in Blood on d + 266 |
|---|---|---|---|---|---|---|---|---|
| 4095 | TRAV4/ TRBV5-6 (A) | CLVGDMDQAGTALIF (SEQ ID NO: 11)/ CASSLGEGRVDGYTF (SEQ ID NO: 14) | 0.21 0.20 0.16 | 20 26 33 | 49.5 | 1 | Not detected | Not applicable |
| 4095 | TRAV12-2/ TRBV10-2 | CAAAMDSSYKLIF (SEQ ID NO: 35)/ CASSDPGTEAFF (SEQ ID NO: 38) | 2.7 3.0 2.9 | 1 1 2 | 19.1 | 2 | 10.4 | 1 |
| 4095 | TRAV4/ TRBV5-6 (B) | CLVGDRDQAGTALIF (SEQ ID NO: 27)/ CASSFGQSSTYGYTF (SEQ ID NO: 30) | Not detected | NA | 6.9 | 3 | 4.5 | 5 |
| 4095 | TRAV4/ TRBV5-6 (C) | CLVGDMDQAGTALIF (SEQ ID NO: 19)/ CASSLGRASNQPQHF (SEQ ID NO: 22) | 0.02 0.01 0.008 | 917 1589 2243 | 0.04 | 45 | 0.005 | 1784 |

†Three different metastatic tumor fragments were evaluated for patient 4095.
d + 266 = 266 days after cell transfer.

TCR alpha constant chain, and introducing a second disulfide bond between the alpha and beta chain constant regions.

TABLE 7

| TCR-α/TCR-β Gene Name | Alpha Chain Amino Acid Sequence | Beta Chain Amino Acid Sequence |
| --- | --- | --- |
| TRAV4/TRBV5-6 (A) | SEQ ID NO: 50 | SEQ ID NO: 51 |
| TRAV12-2/TRBV10-2 | SEQ ID NO: 56 | SEQ ID NO: 57 |
| TRAV4/TRBV5-6 (B) | SEQ ID NO: 54 | SEQ ID NO: 55 |
| TRAV4/TRBV5-6 (C) | SEQ ID NO: 52 | SEQ ID NO: 53 |

Autologous peripheral blood T cells were genetically modified to express one of these four TCRs. Cell surface expression of the introduced TCRs was evaluated on day 10 post-TCR gene modification by flow cytometric analysis for the murine TCR-β constant region (mTCR-β) since the TCRs were designed with the murine TCR-alpha and beta constant regions. Vector transduced cells served as a negative control. The data are gated were gated on CD8+ T cells. The percentage of cells expressing the murine TCR-β constant region are shown in Table 8.

TABLE 8

| Vector Transduced | % |
| --- | --- |
| TRAV4/TRBV5-6 (A) | 83 |
| TRAV12-2/TRBV10-2 | 83 |
| TRAV4/TRBV5-6 (B) | 83 |
| TRAV4/TRBV5-6 (C) | 79 |
| Empty Vector(Control) | 0 |

The TCR-engineered T cells were co-cultured overnight with autologous PBMCs incubated with titrating amounts of KRAS wild-type (WT) or G12D mutant 9mer or 10mer peptides. The percentage of cells expressing the T-cell activation marker 4-1BB was measured. The results are shown in FIGS. 3A-3D. Three of the four TCRs were preferentially reactive against the 9 amino acid long $KRAS^{G12D}$ peptide GADGVGKSA (SEQ ID NO: 8), while one TCR was reactive only against the 10 amino acid long $KRAS^{G12D}$ peptide GADGVGKSAL (SEQ ID NO: 6) (FIGS. 3A-3D). All TCRs were specific for the mutation and did not recognize the wild type KRAS peptides (FIGS. 3A-3D). Peptide titration experiments demonstrated that the TCRs were able to recognize peptides at concentrations between 1-10 nM when pulsed onto autologous PBMCs (FIGS. 3A-3D).

The TCR-engineered T cells were co-cultured overnight with one of two $KRAS^{G12D}$-positive pancreatic cancer cells lines (MDA-Panc48 or HPAC) not expressing or expressing the HLA-C*08:02 allele. IFN-γ secretion was measured by ELISPOT assay and 4-1BB expression was measured by flow cytometry. The results are shown in FIGS. 4A-4B. The TCRs specifically recognized the pancreatic cancer cells lines only when they expressed both the $KRAS^{G12D}$ mutation and the HLA-C*08:02 allele (FIGS. 4A-4B).

Example 3

This example demonstrates that cells transduced to express the TRAV12-2/TRBV10-2 TCR (SEQ ID NOs: 56 and 57) recognize mutated KRAS in the context of HLA allele C*08:02 or C*05:01.

Autologous peripheral blood T cells were genetically modified to express one of the four TCRs as described in Example 2. COS7 cells were co-transfected with full length wild-type (wt) KRAS or KRAS-G12D genes and the HLA allele C*07:01, C*08:02, or C*05:01, followed by co-culture with the indicated $KRAS^{G12D}$-reactive TCR transduced cells. Cells were analyzed for 4-1BB expression by flow cytometry the next day. The results are shown in FIGS. 5A-5D. Data were gated on TCR-transduced (mouse TCRβ+) CD8+ T cells. HLA-C*07:01 served as a negative control HLA allele.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified TCR comprising the amino acid sequences of:
(a) SEQ ID NOs: 9-14;
(b) SEQ ID NOs: 17-22;
(c) SEQ ID NOs: 25-27;
(d) SEQ ID NOs: 28-30;
(e) SEQ ID NOs: 33-35; or
(f) SEQ ID NOs: 36-38.

2. The isolated or purified TCR of claim 1, comprising the amino acid sequences of:
(a) SEQ ID NOs: 9-14;
(b) SEQ ID NOs: 17-22;
(c) SEQ ID NOs: 25-30; or
(d) SEQ ID NOs: 33-38.

3. The isolated or purified TCR of claim 2, comprising:
(i) an amino acid sequence at least 99% identical to the amino acid sequence of SEQ ID NO: 15 and an amino acid sequence at least 99% identical to the amino acid sequence of SEQ ID NO: 16;
(ii) an amino acid sequence at least 99% identical to the amino acid sequence of SEQ ID NO: 15 and an amino acid sequence at least 99% identical to the amino acid sequence of SEQ ID NO: 24;
(iii) an amino acid sequence at least 99% identical to the amino acid sequence of SEQ ID NO: 23 and an amino acid sequence at least 99% identical to the amino acid sequence of SEQ ID NO: 24;
(iv) an amino acid sequence at least 99% identical to the amino acid sequence of SEQ ID NO: 31 and an amino acid sequence at least 99% identical to the amino acid sequence of SEQ ID NO: 32;
(v) an amino acid sequence at least 99% identical to the amino acid sequence of SEQ ID NO: 39 and an amino acid sequence at least 99% identical to the amino acid sequence of SEQ ID NO: 40;
(vi) an amino acid sequence at least 99% identical to amino acids 20-129 of SEQ ID NO: 15 and an amino acid sequence at least 99% identical to amino acids 22-133 of SEQ ID NO: 16;
(vii) an amino acid sequence at least 99% identical amino acids 20-129 of SEQ ID NO: 15 and an amino acid sequence at least 99% identical to amino acids 22-133 of SEQ ID NO: 24;
(viii) an amino acid sequence at least 99% identical to amino acids 20-129 of SEQ ID NO: 23 and an amino acid sequence at least 99% identical to amino acids 22-133 of SEQ ID NO: 24;
(ix) an amino acid sequence at least 99% identical to amino acids 20-129 of SEQ ID NO: 31 and an amino acid sequence at least 99% identical to amino acids 22-133 of SEQ ID NO: 32; or
(x) an amino acid sequence at least 99% identical to amino acids 21-132 of SEQ ID NO: 39 and an amino acid sequence at least 99% identical to the amino acids 22-130 of SEQ ID NO: 40.

4. The isolated or purified TCR of claim 2, comprising:
(i) the amino acid sequences of SEQ ID NOs: 15 and 16;
(ii) the amino acid sequences of SEQ ID NOs:15 and 24;
(iii) the amino acid sequences of SEQ ID NOs: 23 and 24;
(iv) the amino acid sequences of SEQ ID NOs: 31 and 32;
(v) the amino acid sequences of SEQ ID NOs: 39 and 40;
(vi) amino acids 20-129 of SEQ ID NO: 15 and amino acids 22-133 of SEQ ID NO: 16;
(vii) amino acids 20-129 of SEQ ID NO: 15 and amino acids 22-133 of SEQ ID NO: 24;
(viii) amino acids 20-129 of SEQ ID NO: 23 and amino acids 22-133 of SEQ ID NO: 24;
(ix) amino acids 20-129 of SEQ ID NO: 31 and amino acids 22-133 of SEQ ID NO: 32; or
(x) amino acids 21-132 of SEQ ID NO: 39 and amino acids 22-130 of SEQ ID NO: 40.

5. The isolated or purified TCR of claim 2, comprising:
(A) an amino acid sequence at least 99% identical to the amino acid sequence of SEQ ID NO: 46, wherein:
(i) X at position 48 of SEQ ID NO: 46 is Thr or Cys;
(ii) X at position 112 of SEQ ID NO: 46 is Ser, Ala, Val, Leu, Ile, Pro, Phe, Met, or Trp;
(iii) X at position 114 of SEQ ID NO: 46 is Met, Ala, Val, Leu, Ile, Pro, Phe, or Trp;
and
(iv) X at position 115 of SEQ ID NO: 46 is Gly, Ala, Val, Leu, Ile, Pro, Phe, Met, or Trp;
and
(B) an amino acid sequence at least 99% identical to the amino acid sequence of SEQ ID NO: 47, wherein X at position 57 of SEQ ID NO: 47 is Ser or Cys.

6. The isolated or purified TCR of claim 2, comprising:
(A) the amino acid sequence of SEQ ID NO: 46, wherein:
   (i) X at position 48 of SEQ ID NO: 46 is Thr or Cys;
   (ii) X at position 112 of SEQ ID NO: 46 is Ser, Ala, Val, Leu, Ile, Pro, Phe, Met, or Trp;
   (iii) X at position 114 of SEQ ID NO: 46 is Met, Ala, Val, Leu, Ile, Pro, Phe, or Trp;
   and
   (iv) X at position 115 of SEQ ID NO: 46 is Gly, Ala, Val, Leu, Ile, Pro, Phe, Met, or Trp;
and
(B) the amino acid sequence of SEQ ID NO: 47, wherein X at position 57 of SEQ ID NO: 47 is Ser or Cys.

7. The isolated or purified TCR of claim 2, comprising:
(1) an amino acid sequence at least 99% identical to the amino acid sequence of SEQ ID NO: 50 and an amino acid sequence at least 99% identical to the amino acid sequence of SEQ ID NO: 51;
(2) an amino acid sequence at least 99% identical to the amino acid sequence of SEQ ID NO: 52 and an amino acid sequence at least 99% identical to the amino acid sequence of SEQ ID NO: 53;
(3) an amino acid sequence at least 99% identical to the amino acid sequence of SEQ ID NO: 50 and an amino acid sequence at least 99% identical to the amino acid sequence of SEQ ID NO: 53;
(4) an amino acid sequence at least 99% identical to the amino acid sequence of SEQ ID NO: 54 and an amino acid sequence at least 99% identical to the amino acid sequence of SEQ ID NO: 55;
(5) an amino acid sequence at least 99% identical to the amino acid sequence of SEQ ID NO: 56 and an amino acid sequence at least 99% identical to the amino acid sequence of SEQ ID NO: 57;
(6) an amino acid sequence at least 99% identical to amino acids 20-266 of SEQ ID NO: 50 and an amino acid sequence at least 99% identical to amino acids 22-306 of SEQ ID NO: 51;
(7) an amino acid sequence at least 99% identical to amino acids 20-266 of SEQ ID NO: 52 and an amino acid sequence at least 99% identical to amino acids 22-306 of SEQ ID NO: 53;
(8) an amino acid sequence at least 99% identical to amino acids 20-266 of SEQ ID NO: 50 and an amino acid sequence at least 99% identical to amino acids 22-306 of SEQ ID NO: 53;
(9) an amino acid sequence at least 99% identical to amino acids 20-266 of SEQ ID NO: 54 and an amino acid sequence at least 99% identical to amino acids 22-306 of SEQ ID NO: 55; or
(10) an amino acid sequence at least 99% identical to amino acids 21-269 of SEQ ID NO: 56 and an amino acid sequence at least 99% identical to amino acids 22-303 of SEQ ID NO: 57.

8. The isolated or purified TCR of claim 2, comprising:
(1) the amino acid sequences of SEQ ID NOs: 50 and 51;
(2) the amino acid sequences of SEQ ID NOs: 52 and 53;
(3) the amino acid sequences of SEQ ID NOs: 50 and 53;
(4) the amino acid sequences of SEQ ID NOs: 54 and 55;
(5) the amino acid sequences of SEQ ID NOs: 56 and 57;
(6) amino acids 20-266 of SEQ ID NO: 50 and amino acids 22-306 of SEQ ID NO: 51;
(7) amino acids 20-266 of SEQ ID NO: 52 and amino acids 22-306 of SEQ ID NO: 53;
(8) amino acids 20-266 of SEQ ID NO: 50 and amino acids 22-306 of SEQ ID NO: 53;
(9) amino acids 20-266 of SEQ ID NO: 54 and amino acids 22-306 of SEQ ID NO: 55; or
(10) amino acids 21-269 of SEQ ID NO: 56 and amino acids 22-303 of SEQ ID NO: 57.

9. An isolated or purified protein comprising:
(a) a first polypeptide chain comprising the amino acid sequences of SEQ ID NOs: 9-11 and a second polypeptide chain comprising the amino acid sequences of SEQ ID NOs: 12-14;
(b) a first polypeptide chain comprising the amino acid sequences of SEQ ID NOs: 17-19 and a second polypeptide chain comprising the amino acid sequences of SEQ ID NOs: 20-22;
(c) a first polypeptide chain comprising the amino acid sequences of SEQ ID NOs: 9-11 and a second polypeptide chain comprising the amino acid sequences of SEQ ID NOs: 20-22;
(d) a first polypeptide chain comprising the amino acid sequences of SEQ ID NOs: 25-27 and a second polypeptide chain comprising the amino acid sequences of SEQ ID NOs: 28-30; or
(e) a first polypeptide chain comprising the amino acid sequences of SEQ ID NOs: 33-35 and a second polypeptide chain comprising the amino acid sequences of SEQ ID NOs: 36-38.

10. The isolated or purified protein of claim 9, wherein:
(i) the first polypeptide chain comprises an amino acid sequence at least 99% identical to the amino acid sequence of SEQ ID NO: 15 and the second polypeptide chain comprises an amino acid sequence at least 99% identical to the amino acid sequence of SEQ ID NO: 16;
(ii) the first polypeptide chain comprises an amino acid sequence at least 99% identical to the amino acid sequence of SEQ ID NO: 23 and the second polypeptide chain comprises an amino acid sequence at least 99% identical to the amino acid sequence of SEQ ID NO: 24;
(iii) the first polypeptide chain comprises an amino acid sequence at least 99% identical to the amino acid sequence of SEQ ID NO: 15 and the second polypeptide chain comprises an amino acid sequence at least 99% identical to the amino acid sequence of SEQ ID NO: 24;
(iv) the first polypeptide chain comprises an amino acid sequence at least 99% identical to the amino acid sequence of SEQ ID NO: 31 and the second polypeptide chain comprises an amino acid sequence at least 99% identical to the amino acid sequence of SEQ ID NO: 32;
(v) the first polypeptide chain comprises an amino acid sequence at least 99% identical to the amino acid sequence of SEQ ID NO: 39 and the second polypeptide chain comprises an amino acid sequence at least 99% identical to the amino acid sequence of SEQ ID NO: 40;
(vi) the first polypeptide chain comprises an amino acid sequence at least 99% identical to amino acids 20-129 of SEQ ID NO: 15 and the second polypeptide chain comprises an amino acid sequence at least 99% identical to amino acids 22-133 of SEQ ID NO: 16;
(vii) the first polypeptide chain comprises an amino acid sequence at least 99% identical amino acids 20-129 of SEQ ID NO: 15 and the second polypeptide chain comprises an amino acid sequence at least 99% identical to amino acids 22-133 of SEQ ID NO: 24;

(viii) the first polypeptide chain comprises an amino acid sequence at least 99% identical to amino acids 20-129 of SEQ ID NO: 23 and the second polypeptide chain comprises an amino acid sequence at least 99% identical to amino acids 22-133 of SEQ ID NO: 24;

(ix) the first polypeptide chain comprises an amino acid sequence at least 99% identical to amino acids 20-129 of SEQ ID NO: 31 and the second polypeptide chain comprises an amino acid sequence at least 99% identical to amino acids 22-133 of SEQ ID NO: 32; or (x) the first polypeptide chain comprises an amino acid sequence at least 99% identical to amino acids 21-132 of SEQ ID NO: 39 and the second polypeptide chain comprises an amino acid sequence at least 99% identical to the amino acids 22-130 of SEQ ID NO: 40.

11. The isolated or purified protein of claim 9, wherein:

(i) the first polypeptide chain comprises the amino acid sequence of SEQ ID NO: 15 and the second polypeptide chain comprises the amino acid sequence of SEQ ID NO: 16;

(ii) the first polypeptide chain comprises the amino acid sequence of SEQ ID NO: 23 and the second polypeptide chain comprises the amino acid sequence of SEQ ID NO: 24;

(iii) the first polypeptide chain comprises the amino acid sequence of SEQ ID NO: 15 and the second polypeptide chain comprises the amino acid sequence of SEQ ID NO: 24;

(iv) the first polypeptide chain comprises the amino acid sequence of SEQ ID NO: 31 and the second polypeptide chain comprises the amino acid sequence of SEQ ID NO: 32; or (v) the first polypeptide chain comprises the amino acid sequence of SEQ ID NO: 39 and the second polypeptide chain comprises the amino acid sequence of SEQ ID NO: 40;

(vi) the first polypeptide chain comprises amino acids 20-129 of SEQ ID NO: 15 and the second polypeptide chain comprises amino acids 22-133 of SEQ ID NO: 16;

(vii) the first polypeptide chain comprises amino acids 20-129 of SEQ ID NO: 15 and the second polypeptide chain comprises amino acids 22-133 of SEQ ID NO: 24;

(viii) the first polypeptide chain comprises amino acids 20-129 of SEQ ID NO: 23 and the second polypeptide chain comprises amino acids 22-133 of SEQ ID NO: 24;

(ix) the first polypeptide chain comprises amino acids 20-129 of SEQ ID NO: 31 and the second polypeptide chain comprises amino acids 22-133 of SEQ ID NO: 32; or (x) the first polypeptide chain comprises amino acids 21-132 of SEQ ID NO: 39 and the second polypeptide chain comprises amino acids 22-130 of SEQ ID NO: 40.

12. The isolated or purified protein of claim 9, wherein:

(A) the first polypeptide chain comprises an amino acid sequence at least 99% identical to the amino acid sequence of SEQ ID NO: 46, wherein:

(i) X at position 48 of SEQ ID NO: 46 is Thr or Cys;

(ii) X at position 112 of SEQ ID NO: 46 is Ser, Ala, Val, Leu, Ile, Pro, Phe, Met, or Trp;

(iii) X at position 114 of SEQ ID NO: 46 is Met, Ala, Val, Leu, Ile, Pro, Phe, or Trp;

and (iv) X at position 115 of SEQ ID NO: 46 is Gly, Ala, Val, Leu, Ile, Pro, Phe, Met, or Trp;

and (B) the second polypeptide chain comprises an amino acid sequence at least 99% identical to the amino acid sequence of SEQ ID NO: 47, wherein X at position 57 of SEQ ID NO: 47 is Ser or Cys.

13. The isolated or purified protein of claim 9, wherein:

(A) the first polypeptide chain comprises the amino acid sequence of SEQ ID NO: 46, wherein:

(i) X at position 48 of SEQ ID NO: 46 is Thr or Cys;

(ii) X at position 112 of SEQ ID NO: 46 is Ser, Ala, Val, Leu, Ile, Pro, Phe, Met, or Trp;

(iii) X at position 114 of SEQ ID NO: 46 is Met, Ala, Val, Leu, Ile, Pro, Phe, or Trp;

and (iv) X at position 115 of SEQ ID NO: 46 is Gly, Ala, Val, Leu, Ile, Pro, Phe, Met, or Trp;

and (B) the second polypeptide chain comprises the amino acid sequence of SEQ ID NO: 47, wherein X at position 57 of SEQ ID NO: 47 is Ser or Cys.

14. The isolated or purified protein of claim 9, wherein:

(1) the first polypeptide chain comprises an amino acid sequence at least 99% identical to the amino acid sequence of SEQ ID NO: 50 and the second polypeptide chain comprises an amino acid sequence at least 99% identical to the amino acid sequence of SEQ ID NO: 51;

(2) the first polypeptide chain comprises an amino acid sequence at least 99% identical to the amino acid sequence of SEQ ID NO: 52 and the second polypeptide chain comprises an amino acid sequence at least 99% identical to the amino acid sequence of SEQ ID NO: 53;

(3) the first polypeptide chain comprises an amino acid sequence at least 99% identical to the amino acid sequence of SEQ ID NO: 50 and the second polypeptide chain comprises an amino acid sequence at least 99% identical to the amino acid sequence of SEQ ID NO: 53;

(4) the first polypeptide chain comprises an amino acid sequence at least 99% identical to the amino acid sequence of SEQ ID NO: 54 and the second polypeptide chain comprises an amino acid sequence at least 99% identical to the amino acid sequence of SEQ ID NO: 55;

(5) the first polypeptide chain comprises an amino acid sequence at least 99% identical to the amino acid sequence of SEQ ID NO: 56 and the second polypeptide chain comprises an amino acid sequence at least 99% identical to the amino acid sequence of SEQ ID NO: 57;

(6) the first polypeptide chain comprises an amino acid sequence at least 99% identical to amino acids 20-266 of SEQ ID NO: 50 and the second polypeptide chain comprises an amino acid sequence at least 99% identical to amino acids 22-306 of SEQ ID NO: 51;

(7) the first polypeptide chain comprises an amino acid sequence at least 99% identical to amino acids 20-266 of SEQ ID NO: 52 and the second polypeptide chain comprises an amino acid sequence at least 99% identical to amino acids 22-306 of SEQ ID NO: 53;

(8) the first polypeptide chain comprises an amino acid sequence at least 99% identical to amino acids 20-266 of SEQ ID NO: 50 and the second polypeptide chain comprises an amino acid sequence at least 99% identical to amino acids 22-306 of SEQ ID NO: 53;
(9) the first polypeptide chain comprises an amino acid sequence at least 99% identical to amino acids 20-266 of SEQ ID NO: 54 and the second polypeptide chain comprises an amino acid sequence at least 99% identical to amino acids 22-306 of SEQ ID NO: 55; or
(10) the first polypeptide chain comprises an amino acid sequence at least 99% identical to amino acids 21-269 of SEQ ID NO: 56 and the second polypeptide chain comprises an amino acid sequence at least 99% identical to amino acids 22-303 of SEQ ID NO: 57.

15. The isolated or purified protein of claim 9, wherein:
(1) the first polypeptide chain comprises the amino acid sequence of SEQ ID NO: 50 and the second polypeptide chain comprises the amino acid sequence of SEQ ID NO: 51;
(2) the first polypeptide chain comprises the amino acid sequence of SEQ ID NO: 52 and the second polypeptide chain comprises the amino acid sequence of SEQ ID NO: 53;
(3) the first polypeptide chain comprises the amino acid sequence of SEQ ID NO: 50 and the second polypeptide chain comprises the amino acid sequence of SEQ ID NO: 53;
(4) the first polypeptide chain comprises the amino acid sequence of SEQ ID NOs: 54 and the second polypeptide chain comprises the amino acid sequence of SEQ ID NO: 55;
(5) the first polypeptide chain comprises the amino acid sequence of SEQ ID NOs: 56 and the second polypeptide chain comprises the amino acid sequence of SEQ ID NO: 57;
(6) the first polypeptide chain comprises amino acids 20-266 of SEQ ID NO: 50 and the second polypeptide chain comprises amino acids 22-306 of SEQ ID NO: 51;
(7) the first polypeptide chain comprises amino acids 20-266 of SEQ ID NO: 52 and the second polypeptide chain comprises amino acids 22-306 of SEQ ID NO: 53;
(8) the first polypeptide chain comprises amino acids 20-266 of SEQ ID NO: 50 and the second polypeptide chain comprises amino acids 22-306 of SEQ ID NO: 53;
(9) the first polypeptide chain comprises amino acids 20-266 of SEQ ID NO: 54 and the second polypeptide chain comprises amino acids 22-306 of SEQ ID NO: 55; or
(10) the first polypeptide chain comprises amino acids 21-269 of SEQ ID NO: 56 and the second polypeptide chain comprises amino acids 22-303 of SEQ ID NO: 57.

16. An isolated or purified host cell expressing the TCR of claim 2.

17. A population of cells comprising at least one isolated or purified host cell of claim 16.

18. A pharmaceutical composition comprising the TCR of claim 2 and a pharmaceutically acceptable carrier.

19. An isolated or purified TCR that results from expression of a nucleic acid sequence encoding the TCR of claim 2.

20. An isolated or purified host cell comprising the TCR of claim 19.

21. An isolated or purified polypeptide comprising the amino acid sequences of:
(a) SEQ ID NOs: 9-14;
(b) SEQ ID NOs: 17-22;
(c) SEQ ID NOs: 25-27;
(d) SEQ ID NOs: 28-30;
(e) SEQ ID NOs: 33-35; or
(f) SEQ ID NOs: 36-38.

22. The isolated or purified polypeptide of claim 21, comprising the amino acid sequences of:
(a) SEQ ID NOs: 9-14;
(b) SEQ ID NOs: 17-22;
(c) SEQ ID NOs: 25-30; or
(d) SEQ ID NOs: 33-38.

23. The isolated or purified polypeptide of claim 22, comprising:
(i) an amino acid sequence at least 99% identical to the amino acid sequence of SEQ ID NO: 15 and an amino acid sequence at least 99% identical to the amino acid sequence of SEQ ID NO: 16;
(ii) an amino acid sequence at least 99% identical to the amino acid sequence of SEQ ID NO: 15 and an amino acid sequence at least 99% identical to the amino acid sequence of SEQ ID NO: 24;
(iii) an amino acid sequence at least 99% identical to the amino acid sequence of SEQ ID NO: 23 and an amino acid sequence at least 99% identical to the amino acid sequence of SEQ ID NO: 24;
(iv) an amino acid sequence at least 99% identical to the amino acid sequence of SEQ ID NO: 31 and an amino acid sequence at least 99% identical to the amino acid sequence of SEQ ID NO: 32;
(v) an amino acid sequence at least 99% identical to the amino acid sequence of SEQ ID NO: 39 and an amino acid sequence at least 99% identical to the amino acid sequence of SEQ ID NO: 40;
(vi) an amino acid sequence at least 99% identical to amino acids 20-129 of SEQ ID NO: 15 and an amino acid sequence at least 99% identical to amino acids 22-133 of SEQ ID NO: 16;
(vii) an amino acid sequence at least 99% identical amino acids 20-129 of SEQ ID NO: 15 and an amino acid sequence at least 99% identical to amino acids 22-133 of SEQ ID NO: 24;
(viii) an amino acid sequence at least 99% identical to amino acids 20-129 of SEQ ID NO: 23 and an amino acid sequence at least 99% identical to amino acids 22-133 of SEQ ID NO: 24;
(ix) an amino acid sequence at least 99% identical to amino acids 20-129 of SEQ ID NO: 31 and an amino acid sequence at least 99% identical to amino acids 22-133 of SEQ ID NO: 32; or
(x) an amino acid sequence at least 99% identical to amino acids 21-132 of SEQ ID NO: 39 and an amino acid sequence at least 99% identical to the amino acids 22-130 of SEQ ID NO: 40.

24. The isolated or purified polypeptide of claim 22, comprising:
(i) the amino acid sequences of SEQ ID NOs: 15 and 16;
(ii) the amino acid sequences of SEQ ID NOs: 15 and 24;
(iii) the amino acid sequences of SEQ ID NOs: 23 and 24;
(iv) the amino acid sequences of SEQ ID NOs: 31 and 32;
(v) the amino acid sequences of SEQ ID NOs: 39 and 40;
(vi) amino acids 20-129 of SEQ ID NO: 15 and amino acids 22-133 of SEQ ID NO: 16;
(vii) amino acids 20-129 of SEQ ID NO: 15 and amino acids 22-133 of SEQ ID NO: 24;

(viii) amino acids 20-129 of SEQ ID NO: 23 and amino acids 22-133 of SEQ ID NO: 24;
(ix) amino acids 20-129 of SEQ ID NO: 31 and amino acids 22-133 of SEQ ID NO: 32; or
(x) amino acids 21-132 of SEQ ID NO: 39 and amino acids 22-130 of SEQ ID NO: 40.

25. The isolated or purified polypeptide of claim 22, comprising:
(A) an amino acid sequence at least 99% identical to the amino acid sequence of SEQ ID NO: 46, wherein:
(i) X at position 48 of SEQ ID NO: 46 is Thr or Cys;
(ii) X at position 112 of SEQ ID NO: 46 is Ser, Ala, Val, Leu, Ile, Pro, Phe, Met, or Trp;
(iii) X at position 114 of SEQ ID NO: 46 is Met, Ala, Val, Leu, Ile, Pro, Phe, or Trp; and
(iv) X at position 115 of SEQ ID NO: 46 is Gly, Ala, Val, Leu, Ile, Pro, Phe, Met, or Trp; and
(B) an amino acid sequence at least 99% identical to the amino acid sequence of SEQ ID NO: 47, wherein X at position 57 of SEQ ID NO: 47 is Ser or Cys.

26. The isolated or purified polypeptide of claim 22, comprising:
(A) the amino acid sequence of SEQ ID NO: 46, wherein:
(i) X at position 48 of SEQ ID NO: 46 is Thr or Cys;
(ii) X at position 112 of SEQ ID NO: 46 is Ser, Ala, Val, Leu, Ile, Pro, Phe, Met, or Trp;
(iii) X at position 114 of SEQ ID NO: 46 is Met, Ala, Val, Leu, Ile, Pro, Phe, or Trp; and
(iv) X at position 115 of SEQ ID NO: 46 is Gly, Ala, Val, Leu, Ile, Pro, Phe, Met, or Trp; and
(B) the amino acid sequence of SEQ ID NO: 47, wherein X at position 57 of SEQ ID NO: 47 is Ser or Cys.

27. The isolated or purified polypeptide of claim 22, comprising:
(1) an amino acid sequence at least 99% identical to the amino acid sequence of SEQ ID NO: 50 and an amino acid sequence at least 99% identical to the amino acid sequence of SEQ ID NO: 51;
(2) an amino acid sequence at least 99% identical to the amino acid sequence of SEQ ID NO: 52 and an amino acid sequence at least 99% identical to the amino acid sequence of SEQ ID NO: 53;
(3) an amino acid sequence at least 99% identical to the amino acid sequence of SEQ ID NO: 50 and an amino acid sequence at least 99% identical to the amino acid sequence of SEQ ID NO: 53;
(4) an amino acid sequence at least 99% identical to the amino acid sequence of SEQ ID NO: 54 and an amino acid sequence at least 99% identical to the amino acid sequence of SEQ ID NO: 55;
(5) an amino acid sequence at least 99% identical to the amino acid sequence of SEQ ID NO: 56 and an amino acid sequence at least 99% identical to the amino acid sequence of SEQ ID NO: 57;
(6) an amino acid sequence at least 99% identical to amino acids 20-266 of SEQ ID NO: 50 and an amino acid sequence at least 99% identical to amino acids 22-306 of SEQ ID NO: 51;
(7) an amino acid sequence at least 99% identical to amino acids 20-266 of SEQ ID NO: 52 and an amino acid sequence at least 99% identical to amino acids 22-306 of SEQ ID NO: 53;
(8) an amino acid sequence at least 99% identical to amino acids 20-266 of SEQ ID NO: 50 and an amino acid sequence at least 99% identical to amino acids 22-306 of SEQ ID NO: 53;
(9) an amino acid sequence at least 99% identical to amino acids 20-266 of SEQ ID NO: 54 and an amino acid sequence at least 99% identical to amino acids 22-306 of SEQ ID NO: 55; or
(10) an amino acid sequence at least 99% identical to amino acids 21-269 of SEQ ID NO: 56 and an amino acid sequence at least 99% identical to amino acids 22-303 of SEQ ID NO: 57.

28. The isolated or purified polypeptide of claim 22, comprising:
(1) the amino acid sequences of SEQ ID NOs: 50 and 51;
(2) the amino acid sequences of SEQ ID NOs: 52 and 53;
(3) the amino acid sequences of SEQ ID NOs: 50 and 53;
(4) the amino acid sequences of SEQ ID NOs: 54 and 55;
(5) the amino acid sequences of SEQ ID NOs: 56 and 57;
(6) amino acids 20-266 of SEQ ID NO: 50 and amino acids 22-306 of SEQ ID NO: 51;
(7) amino acids 20-266 of SEQ ID NO: 52 and amino acids 22-306 of SEQ ID NO: 53;
(8) amino acids 20-266 of SEQ ID NO: 50 and amino acids 22-306 of SEQ ID NO: 53;
(9) amino acids 20-266 of SEQ ID NO: 54 and amino acids 22-306 of SEQ ID NO: 55; or
(10) amino acids 21-269 of SEQ ID NO: 56 and amino acids 22-303 of SEQ ID NO: 57.

29. A method of detecting the presence of a KRAS G12D-expressing cancer in a mammal, the method comprising:
(a) contacting a sample comprising cells of the cancer with the TCR of claim 2, thereby forming a complex; and
(b) detecting the complex,
wherein detection of the complex is indicative of the presence of the KRAS G12D-expressing cancer in the mammal.

30. The method of claim 29, wherein the KRAS G12D-expressing cancer is pancreatic, colorectal, lung, endometrial, ovarian, or prostate cancer.

31. A method of treating a KRAS G12D-expressing cancer in a mammal, comprising administering to the mammal the TCR of claim 2 in an amount effective to treat the KRAS G12D-expressing cancer in the mammal.

32. The method of claim 31, wherein the KRAS G12D-expressing cancer is pancreatic, colorectal, lung, endometrial, ovarian, or prostate cancer.

33. A method of producing the TCR of claim 19, comprising culturing a host cell comprising a recombinant expression vector encoding the TCR of claim 19 so that the TCR is produced.

34. A method of producing a host cell expressing the TCR of claim 19, comprising introducing into a host cell a recombinant expression vector encoding the TCR of claim 19.

35. A method of treating a KRAS G12D-expressing cancer in a mammal, comprising administering to the mammal the TCR of claim 19 in an amount effective to treat the KRAS G12D-expressing cancer in the mammal.

36. A method of treating a KRAS G12D-expressing cancer in a mammal, comprising administering to the mammal the host cell of claim 20 in an amount effective to treat the KRAS G12D-expressing cancer in the mammal.

* * * * *